United States Patent
Kuo et al.

(10) Patent No.: US 10,704,026 B2
(45) Date of Patent: Jul. 7, 2020

(54) EX VIVO CULTURE, PROLIFERATION AND EXPANSION OF INTESTINAL EPITHELIUM

(71) Applicant: The Board of Trustees of the Leland Stanford Junior University, Stanford, CA (US)

(72) Inventors: Calvin Jay Kuo, Palo Alto, CA (US); Akifumi Ootani, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/822,687

(22) Filed: Aug. 10, 2015

(65) Prior Publication Data

US 2015/0344849 A1    Dec. 3, 2015

Related U.S. Application Data

(62) Division of application No. 12/545,755, filed on Aug. 21, 2009, now Pat. No. 9,464,275.

(60) Provisional application No. 61/189,853, filed on Aug. 21, 2008.

(51) Int. Cl.
*C12N 5/071* (2010.01)
*C12N 5/00* (2006.01)
*G01N 33/50* (2006.01)

(52) U.S. Cl.
CPC ......... *C12N 5/0679* (2013.01); *C12N 5/0012* (2013.01); *G01N 33/5005* (2013.01); *G01N 33/5073* (2013.01); *C12N 2501/415* (2013.01); *C12N 2533/54* (2013.01)

(58) Field of Classification Search
None
See application file for complete search history.

(56) References Cited

U.S. PATENT DOCUMENTS

| 2003/0166274 | A1  |  9/2003 | Hewitt |
| 2004/0175367 | A1* |  9/2004 | Herlyn ............. A61K 35/38 424/93.7 |
| 2005/0256036 | A1  | 11/2005 | Boyle et al. |

FOREIGN PATENT DOCUMENTS

| WO | 03/023018 A2 | 3/2003 | |
| WO | WO 2006/136953 | * 12/2006 | ............... C12N 5/06 |
| WO | WO 2008/088524 | * 7/2008 | .............. A61K 38/17 |

OTHER PUBLICATIONS

Sambruy et al., "Intestinal Cell Culture Models", Cell Biology and Toxicology, 2001, vol. 17, pp. 301-317.*
Menard et al., "Explant Culture ofHuman Fetal Small Intestine", Gastroenterology 1985, vol. 88, pp. 691-700.*
Kim et al., "Mitogenic Influence of Human R-Spondin1 on the Intestinal Epithelium", Science. 2005, vol. 309, pp. 1256-1259.*
Ootani et al., "An Air-Liquid Interface Promotes the Differentiation of Gastric Suface Mucous Cells (GSM06) in Culture", Biochemical and Biophysical Research Commiunications, 2000, vol. 271, pp. 741-746.*
Fulcher et al., "Well-differentiated human airway epithelial cell cultures", Methods of Molecular medicine, 2005, vol. 107, pp. 183-206.*
Quinlan et al., "In vitro culture of embryonic mouse intestinal epithelium: cell differentiation and introduction of reporter genes", BMC Developmental Biology, May 2006, pp. 1-11.*
Li et al., "Oncogenic transformation of diverse gastrointestinal tissues in primary organoid culture", Nature Medicine, 2014, pp. 1-26.
Toda et al., "Culture Models for Studying Thyroid Biology and Disorders", ISRN Endocrinology, 2011, vol. 2011, pp. 1-9.
Bartsch; et al., "Establishment of a Long-Term Culture System for Rat Colon Epithelial Cells.", In Vitro Cell Dev Biol. Anim., 2004 Sep.-Oct. 2004; 40(8-9):278-84.
Baten; et al., "Long-term Culture of Norman Human Clonic Epithelial Cells In Vitro", The FASEB Journal, Jun. 1992;6(9):2726-34.
MaCartney; et al., "Primary Murine Small Intestinal Epithelial Cells, Maintained in Long-Term Culture, Are Susceptible to Rotavirus Infection.", Jour. of Virology, Jun. 2000; 74(12):5597-5603.
Oottani; et al., "Sustained in Vitro Intestinal Epithelial Culture Within a Wnt-Dependent Stem Cell Niche." Nat. Med., Jun. 2009; 15(6):701-706.
Panja; et al., "A Novel Method for the Establishment of a Pure Population of Nontransformed Human Intestinal Primary Epithelial Cell (HIPEC) Lines in Long Term Culture.", Lab Invest., Jun. 2000; 80(9):1473-5.
Rizvi; et at., "Epithelial Stem Cells and Their Niche.", Stem Cells, (2005), 23:150-165.
Sambuy; et al., "Formation of Organoid Structures and Extracellular Matrix Production in an Intestinal Epithelial Cell Line During Long-Term In Vitro Culture.", Cell Differ, Sep. 1986; 9(2):139-47.
Toda; et al., "Thyroid Tissue-Organotypic Culture Using a New Approach for Overcoming the Disadvantage of Conventional Organ Culture.", Cell Biology, (2005), A Laboratory Handbook, vol. 1, Chapter 50.
Toda; et al., "A new Organotypic Culture of Thyroid Tissue Maintains Three-Dimensional Follicles with C Cells for a Long Term.", Bio. Biophysical Research Comm., (2002), 294:906-911.

(Continued)

*Primary Examiner* — Laura Schuberg
(74) *Attorney, Agent, or Firm* — Pamela J. Sherwood; Bozicevic, Field & Francis LLP

(57) ABSTRACT

Methods are provided for long term culture of mammalian intestinal cells. Cultures are initiated with fragments of mammalian intestinal tissue, which are then maintained embedded in a gel substrate that provides an air-liquid interface. Intestinal epithelium in cultures of the invention can be continuously grown for extended periods of time. Mammalian intestinal cells cultured by the methods of the invention recapitulate features of intestinal growth in vivo.

7 Claims, 15 Drawing Sheets

(2 of 15 Drawing Sheet(s) Filed in Color)

(56) References Cited

OTHER PUBLICATIONS

Toda; et al., "Air Exposure Promotes Fibroblast Growth with Increased Expression of Mitogen-Activated Protein . Kinase Cascade.", Bio. Biophysical Research Comm, (2000), 270:961-966.

* cited by examiner

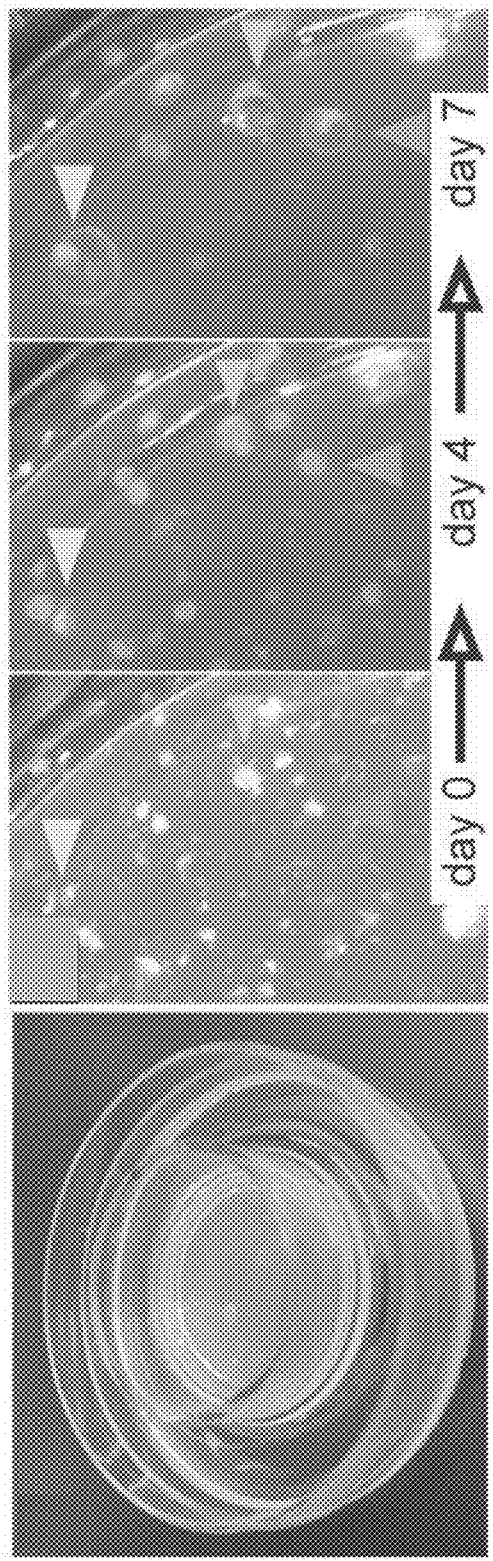
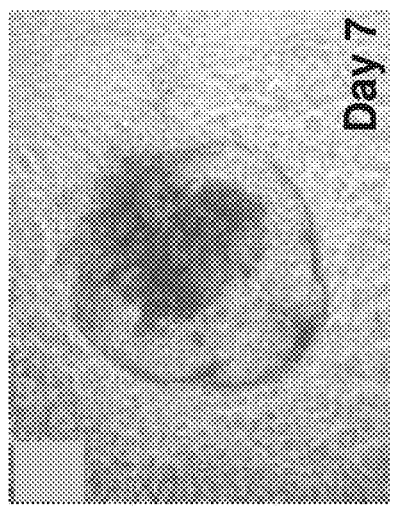
Fig. 2A
Culture of Intestinal Mucosa    Fig. 2B
day 0    day 4    day 7
Fig. 2C Electron Micrographs of Intestinal Explants Goblet cell Endocrine granule Absorpive cells Outer lining myofibroblasts

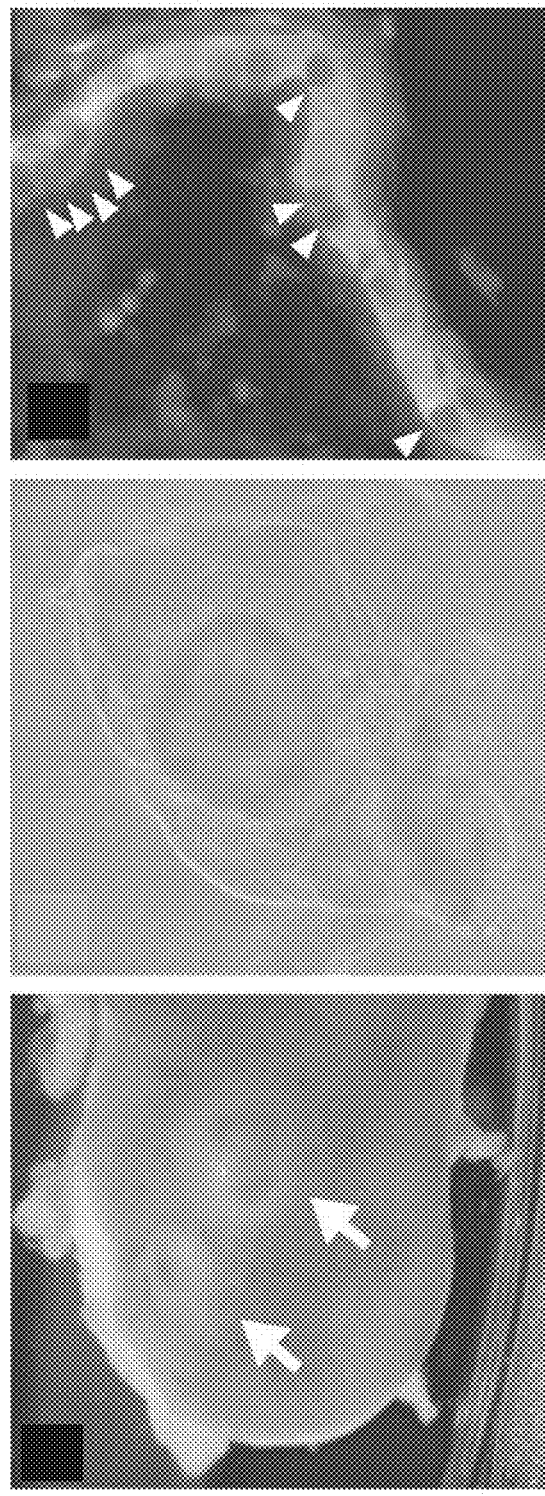

Effect of Wnt agonist and antagonist on intestinal explants

Vehicle

R-Spo1

Dkk1

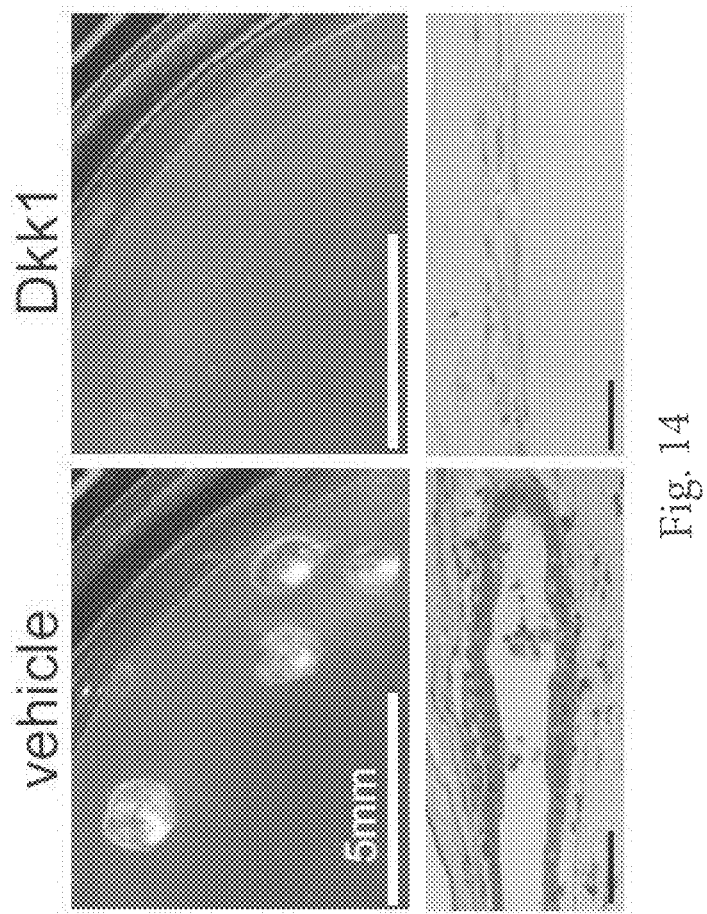

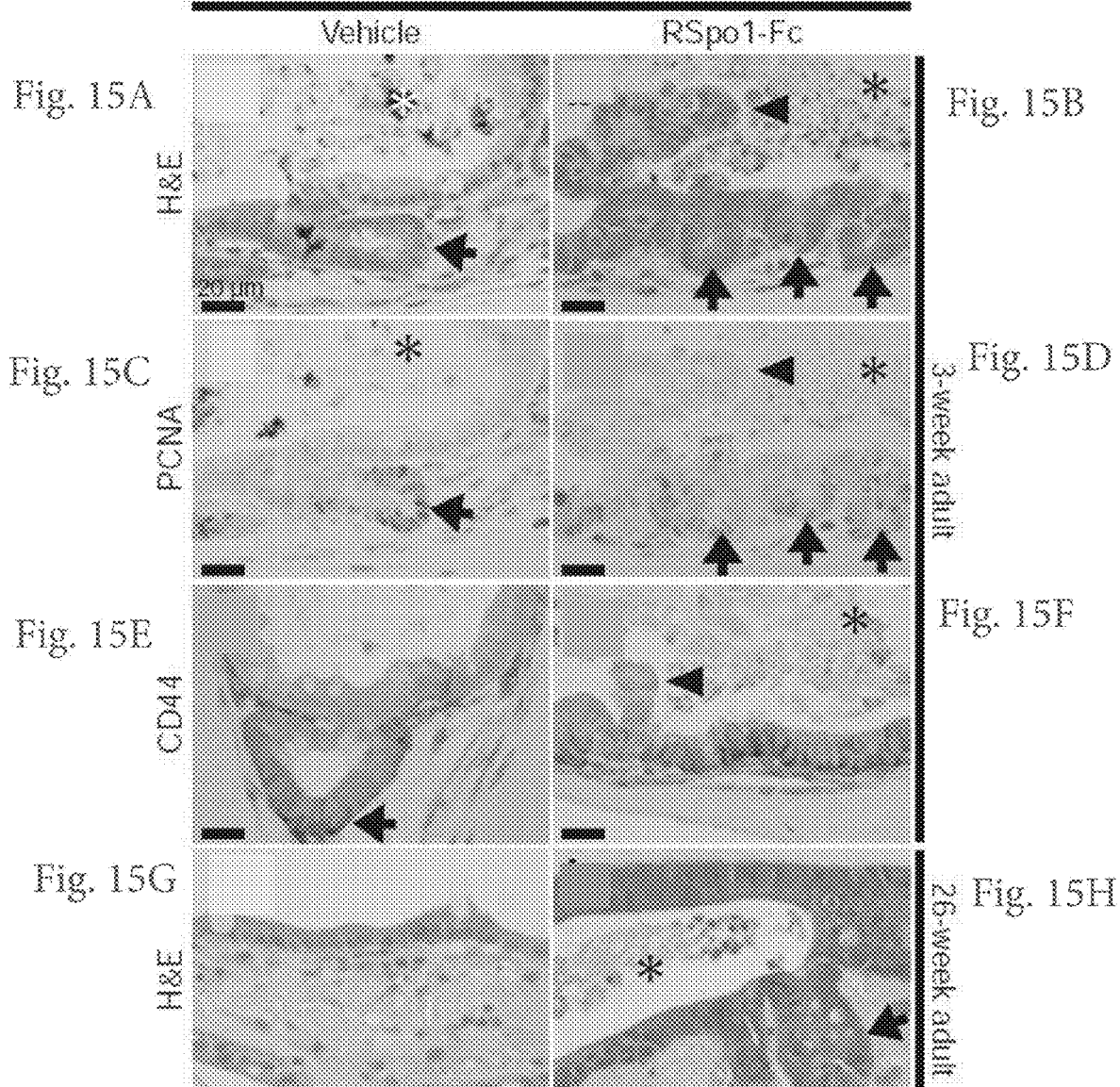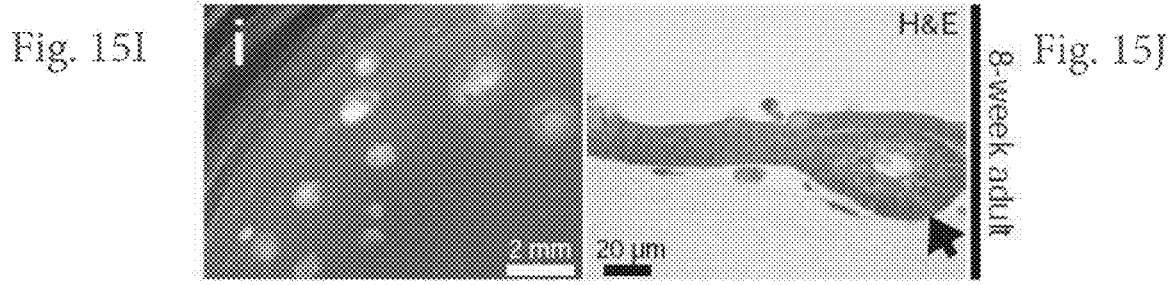

EX VIVO CULTURE, PROLIFERATION AND EXPANSION OF INTESTINAL EPITHELIUM

FEDERALLY SPONSORED RESEARCH AND DEVELOPMENT

This invention was made with Government support under contract DK069989 awarded by the National Institutes of Health. The Government has certain rights in the invention.

BACKGROUND OF THE INVENTION

The roughly 8 meters of intestine in the adult human plays numerous roles in physiologic homeostasis including absorptive, secretory and immune functions. Commensurate with these essential roles, diseases of the intestine are a considerable source of human morbidity and mortality. Indeed, numerous pathologic conditions including inflammatory bowel diseases, mesenteric ischemia, congenital syndromes and trauma, with or without concomitant intestinal resection, result in "short-gut" syndromes resulting in severe deficiencies of physiologic intestinal function and effective intestinal failure. While enhanced regeneration and/or frank tissue engineering of the intestine is highly desirable in these conditions, no established procedures currently allow robust ex vivo expansion of intestinal epithelium or stem/progenitor cells thereof. Consequently, therapies have currently relied on supportive measures such as total parenteral nutrition, in which all nutrition is provided intravenously, or intestinal transplantation.

The intestine is an organ with tremendous regenerative potential, whereby stem cells resident in proliferative crypt regions give rise to progenitors capable of multilineage differentiation. The intestinal stem cells (ISCs) are able to repopulate epithelium of the entire 8-meter length of the adult human intestine every 5-7 days, helping to maintain the integrity of the mucosal barrier and effecting tissue repair upon injury. It has been postulated that the ISC niche has complex architectural requirements whereby myofibroblasts enveloping the proliferative crypt provide essential signals to crypt stem and/or progenitor cells.

A significant impediment to restorative intestinal regeneration for therapeutic purposes has been a lack of clear understanding of the signals regulating self-renewal and proliferation of intestinal stem and progenitor cells, although progress has been made with the identification of the role of Wnt signaling; and the ability of R-spondin1 (RSpo1) to strongly induce intestinal proliferation in vivo.

A second and perhaps more significant impediment to intestinal tissue engineering has been a notable lack of in vitro culture systems allowing the growth of intestinal epithelial cells for more than about 10 days.

Relevant Literature

A number of publications discuss various methods for culturing different cell types including intestinal epithelial cells. Toda et al in Cell Biology: A Laboratory Handbook, Vol. 1, Chapter 50, describe thyroid tissue-organotypic culture using an approach for overcoming the disadvantages of conventional organ culture. The teachings of the culture methods of Toda et al are hereby incorporated by reference. Establishment of a long-term culture system for rat colon epithelial cells is described by Bartsch et al in In Vitro Cell Dev Biol Anim. 2004 September-October; 40(8-9):278-84. Panja et al in Lab Invest. 2000 September; 80(9):1473-5 describe a method for the establishment of a pure population of nontransformed human intestinal primary epithelial cell (HIPEC) lines in long term culture. A method for long-term culture of primary small intestinal epithelial cells (IEC) from suckling mice is described by Macartney et al in J Virol. 2000 June; 74(12):5597-603. Baten et al discuss methods for long-term culture of normal human colonic epithelial cells in vitro. Sambuy; De Angelis I in Cell Differ. 1986 September; 19(2):139-47 describe formation of organoid structures and extracellular matrix production in an intestinal epithelial cell line during long-term in vitro culture.

Methods for differentiating intestinal stem cells and for screening for compositions affecting differentiation have been described. Wobus et al in WO03023018A2 describe a method for isolating, culturing and differentiating intestinal stem cells for therapeutic use. Boyle et al in US20050256036A1 titled "Gastrointestinal proliferative factor and uses thereof" discuss use of pharmaceutical compositions to prevent or treat conditions associated with degeneration of epithelial mucosa.

SUMMARY OF THE INVENTION

Methods are provided for long term culture of mammalian intestinal cells. Cultures are initiated with fragments of mammalian intestinal tissue, which are then maintained embedded in a gel substrate that provides an air-liquid interface. Intestinal epithelium in cultures of the invention can be continuously grown for extended periods of time, e.g. for up to about 15 days, for up to about 1 month, or up to about 2 months, or up to about 3 months or more. Mammalian intestinal cells cultured by the methods of the invention recapitulate features of intestinal growth in vivo. Features include, without limitation, recapitulation of cellular ultrastructure, presence of enterocytes, goblet and enteroendocrine cells, and Wnt-dependent proliferation. While the culture system provides for growth of the varied cells found in normal intestinal lineages, and intestinal stem cells, the cultures are also useful in the generation of cells for selection, to provide purified population or enriched populations of a single lineage including intestinal stem cells.

The cultured cells may be experimentally modified prior, or during the culture period. In some embodiments, the intestinal explant cells are modified by exposure to viral or bacterial pathogens. In other embodiments the cells are modified by altering patterns of gene expression, e.g. by providing reprogramming factors to induce pluripotency or otherwise alter differentiation potential; or by introducing factors that provide for oncogenic transformation of intestinal cells into carcinomas, e.g. APC; Kras; p53; etc. The experimentally modified cells are useful for investigation of the effects of therapeutic agents for anti-viral or anti-bacterial activity; for tumor therapy, for effects on differentiation, and the like. For example, the effect of a gain or loss of gene activity on the ability of cells to form an explant culture may be determined, or on the ability to undergo tumor transformation.

In another aspect of the invention, a method is provided for in vitro screening for agents for their effect on intestinal cells, including processes of cancer initiation and treatment, and including the use of experimentally modified cultures described above. Intestinal explants cultured by the methods described herein are exposed to candidate agents. Agents of interest include pharmaceutical and genetic agents, e.g. antisense, expressible coding sequences, RNAi, and the like, where the genetic agents may correspond to candidate tumor suppressors, candidate oncogenes, and the like. In some embodiments, the effect on intestinal stem cells is determined. In other embodiments the effect of transformation or growth of tumor cells is determined, for example where agents may include, without limitation, chemotherapy, monoclonal antibodies or other protein-based agents, radiation/radiation sensitizers, cDNA, siRNA, shRNA, small molecules, and the like. Agents active on intestinal stem cells are detected by change in growth of the intestinal explants and by the presence of multilineage differentiation markers indicative of intestinal stem cells. In addition, active agents are detected by analyzing intestinal explants for long-term reconstitutive activity. Methods are also provided for using the intestinal explant culture to screen for agents that modulate intestinal transporters 121313141415151616171717I Methods are provided for screening cells in a population, e.g. a Methods are provided for screening cells in a population, e.g. a complex population of multiple cells types, a population of purified cells isolated from a complex population by sorting, culture, etc., and the like, for the presence of cells having intestinal stem cell potential. This method entails co-culture of detectably labeled candidate cells with the intestinal explant culture of the invention. Candidate cells with intestinal stem cell potential are detected by an increase in growth of the intestinal epithelial culture above basal levels and colocalization of multilineage differentiation markers (indicative of presence of intestinal stem cells) with the labeled candidate cells. Stem cell characteristics of candidate cells co-cultured with intestinal explants are further assayed by determining long-term reconstitutive activity, via in vivo transplantation, etc. Candidate intestinal stem cells may be positive for expression of the marker LGR5.

In yet another embodiment of the invention, an assay system for screening for inhibitors of Notch/γ-secretase activity in the intestinal explants is provided. Agents to be screened for this activity are introduced in the culture system. Inhibition of Notch/γ-secretase activity is assayed by the conversion of proliferative crypt cells into goblet cells.

In another aspect of the invention, a method is provided for in vitro screening of agents for cytotoxicity in the intestinal epithelial cell cultures. In yet another embodiment, a method is provided to assess drug absorption by the intestinal epithelial cells of the explant cultures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A-2C. Culture of intestinal tissue. (FIG. 2A) The set up useful for intestinal epithelial culture comprises an outer container with media, an inner container with intestinal tissue in a gel substrate. Intestinal tissue grows as hollow cysts. (FIG. 2B) Increase in size of the cysts from day 0, to day 4, to day 7. (FIG. 2C) Phase-contrast microscopic view of intestinal explant.

(FIG. 4A) The wall of intestinal sphere consists of epithelial monolayer with outer lining myofibroblasts. (FIG. 4B) Alcian blue-positive goblet cells. (FIG. 4C) Grimelius-positive enteroendocrine cells. (FIG. 4D) PCNA-positive proliferative cells. Arrows indicate PCNA-negative differentiated cells.

(FIG. 5A) Highly differentiated epithelial monolayer including enterocytes, goblet cells, and enteroendocrine cells with outer lining myofibroblasts. (FIG. 5B) Brush border. (FIG. 5C) Goblet cells. (FIG. 5D) Outer lining myofibroblasts. (FIG. 5E) Dense enteroendocrine granules beneath the nuclei.

FIG. 6A-6C. Transplantation of cultured intestinal cells from actin-GFP mice under the renal capsule. (FIG. 6A) Arrows indicate significant in vivo expansion of explants for 30 days. (FIG. 6B) GFP-positivity of transplanted intestinal explants. (FIG. 6C) Transplanted intestinal spheres demonstrate a differentiated GFP-positive epithelial monolayer. Arrowheads indicate mucin-positive goblet cells.

(FIG. 7A) Vehicle. (FIG. 7B) R-Spondin1 treatment (500 ng/ml) once a week. (FIG. 7C) Dkk1 treatment (50 µg/ml) during first seven days.

FIG. 12A, The viable cells demonstrate a mosaic fluorescence pattern at d3. (FIG. 12B) By d8, viable cells form sphere-like structures with expanding growth. The sphere epithelium of demonstrates segmental color. (FIG. 12C) At d15, the epithelial cells demonstrate red and green fluorescence and outer lining myofibroblasts express yellow fluorescence. Bars, 100 μm. FIG. 12D-12I, Sections of tetrachimeric intestinal spheres (culture day 32) demonstrate clonal populations. Red: mCherry-expressing cells; green: EGFP-expressing cells; blue: ECFP expressing cells; orange: mOrange-expressing cells. Merged images are shown. (d-g) Jejunal tetrachimeric cultures exhibit distinct clonal domains of fluorescence. (FIG. 12H, FIG. 12I) Colonic tetrachimeric cultures demonstrate red and blue fluorescence, while mesenchymal cells express green and yellow fluorescence. The epithelial cells form multiple crypt-like structures with a single color. The underlining myofibroblasts express EGFP.

FIG. 14. Intestinal stem cells and their Wnt dependency in explant culture Transient Dkk1 treatment ablates subsequent long-term regrowth of explant cultures. Jejunal explants were incubated with Dkk1 (50 μg/ml) or vehicle for 7 days, followed by incubation without Dkk1 for an additional 35d. No growth of intestinal spheres was observed in Dkk1-treatment explants despite subsequent prolonged culture without Dkk1. Note the selective absence of intestinal epithelium and the persistence of mesenchymal fibroblast growth in the Dkk1-treated explant culture (bottom right panel).

FIG. 15A-15H. Explants derived from adult intestinal tissue. (FIG. 15A-15H) Histology of jejunal culture at day 7 from 3-week-old (FIG. 15A-15F) or 26-week old mice (FIG. 15G, FIG. 15H). Staining for H&E (FIG. 15A,15B,15G, 15H), PCNA (FIG. 15C,15D or CD44 (FIG. 15E,15F) is depicted. (FIG. 15I,15J) RSpo1-Fc treatment permitted longer term jejunal cultures (day 28) from 8-week-old adult intestine. Stereomicroscopy (FIG. 15I) and H&E staining (FIG. 15J) is depicted. Arrows indicate highly proliferative PCNA+ crypt-like structures, which invaginated from the sphere wall into the surrounding collagen matrix. Arrowheads indicate quiescent PCNA– villus-like protrusions. Numerous sludged or dead cells are present in the sphere lumen, indicated by the asterisk.

DEFINITIONS

Figure 1:
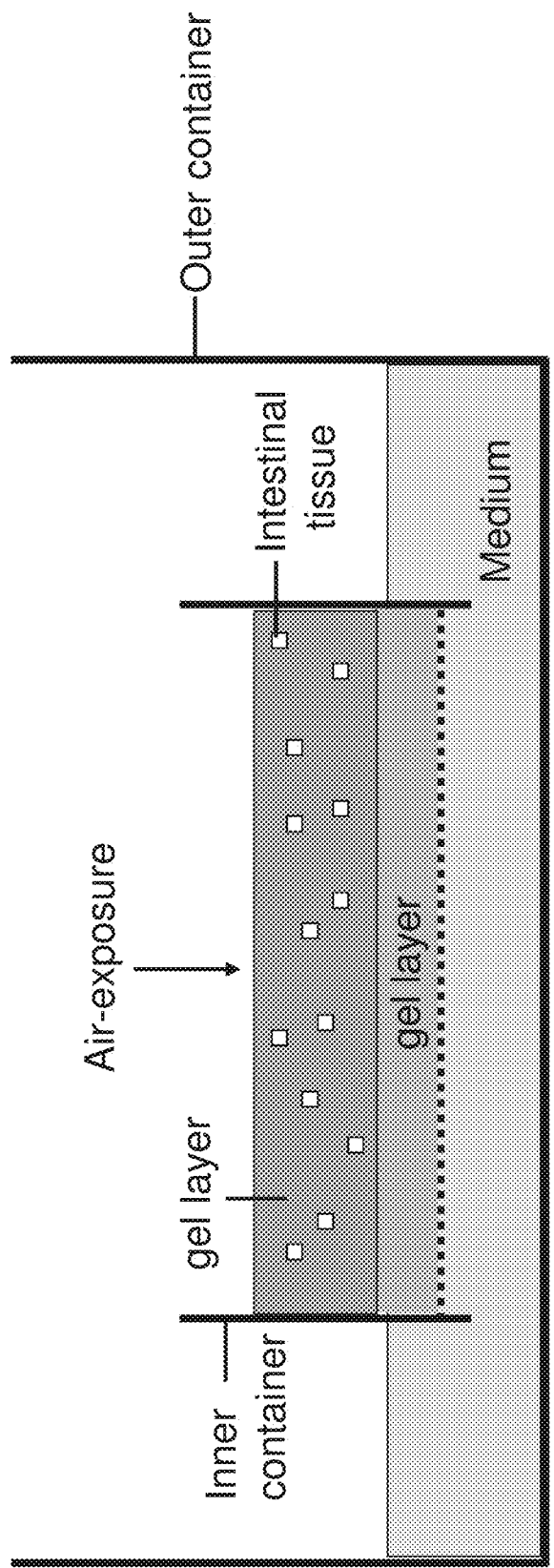
FIG. 1. Schematic of intestinal epithelial cell culture system. The intestinal tissue is mixed with a gel solution which is then poured over a layer of gel formed in container with a lower semi-permeable support, e.g. a membrane. This dish is placed in an outer dish that contains cell culture medium. The level of the medium is maintained such that the gel containing the tissue in not submerged in the medium. The intestinal cells are exposed to air from the top and to liquid medium from the bottom.

In the description that follows, a number of terms conventionally used in the field of cell culture are utilized extensively. In order to provide a clear and consistent understanding of the specification and claims, and the scope to be given to such terms, the following definitions are provided.

The term "cell culture" or "culture" means the maintenance of cells in an artificial, in vitro environment. It is to be understood, however, that the term "cell culture" is a generic term and may be used to encompass the cultivation not only of individual cells, but also of tissues or organs.

A "long term culture" used herein refers to a culture in which intestinal cells grow, differentiate and are viable for at least about 10 days, or more than 30 days, or more than 60 days, or more than 100 days or more than 150 days.

The term "intestinal cells" used herein denotes cells that make up the mammalian intestinal epithelium. The mammalian intestinal epithelium of the gastrointestinal tract has a well-defined organizational structure. The epithelium can be divided into two regions, a functional region that houses differentiated cells (villi) and a proliferative region (crypts of Lieberkuhn) that represents the epithelium stem cell niche. Multipotent epithelium stem cells reside in the crypts and give rise to four principal epithelial lineages: absorptive enterocytes, mucin secreting goblet cells, peptide hormone secreting enteroendocrine cells, and Paneth cells.

The phrase "mammalian intestinal cells" means cells originating from mammalian intestine. Typically, in the methods of the invention pieces of intestine are obtained surgically and minced to a size less than about 1 mm$^3$, and may be less than about 0.5 mm$^3$, or less than about 0.1 mm$^3$. Mammalian used herein includes human, equine, bovine, porcine, canine, feline, rodent, e.g. mice, rats, hamster, primate, etc. Intestinal tissue can be obtained from humans by biopsy during endoscopy. "Mammalian intestinal cells" and "intestinal cells" and "intestinal epithelial cells" have been used interchangeably. The source of the intestinal tissue can be fetus, neonate, juvenile, or adult.

"Intestine" refers to the mammalian small intestine and mammalian large intestine. For the methods described herein the intestinal tissue is obtained either from the small or from the large intestine.

The term "explant" means cells originating from mammalian intestinal tissue, and grown from in vitro, for example according to the methods of the invention.

"Intestinal stem cells" is used interchangeably with "epithelial stem cells" means stem cells that have the potential to proliferate and differentiate into intestinal epithelial cells. Multipotent epithelial stem cells give rise to various epithelial lineages, and may give rise to all intestinal epithelial lineages, which include: absorptive enterocytes, mucin secreting-goblet cells, peptide hormone secreting enteroendocrine cells, and Paneth cells.

Stem cell: The term stem cell is used herein to refer to a mammalian cell that has the ability both to self-renew, and to generate differentiated progeny (see Morrison et al. (1997) Cell 88:287-298). Generally, stem cells also have one or more of the following properties: an ability to undergo asynchronous, or asymmetric replication, that is where the two daughter cells after division can have different phenotypes; extensive self-renewal capacity; capacity for existence in a mitotically quiescent form; and clonal regeneration of all the tissue in which they exist, for example the ability of hematopoietic stem cells to reconstitute all hematopoietic lineages. "Progenitor cells" differ from stem cells in that they typically do not have the extensive self-renewal capacity, and often can only regenerate a subset of the lineages in the tissue from which they derive, for example only lymphoid, or erythroid lineages in a hematopoietic setting.

Stem cells may be characterized by both the presence of markers associated with specific epitopes identified by antibodies and the absence of certain markers as identified by the lack of binding of specific antibodies. Stem cells may also be identified by functional assays both in vitro and in vivo, particularly assays relating to the ability of stem cells to give rise to multiple differentiated progeny.

Stem cells and cultures thereof: Pluripotent stem cells are cells derived from any kind of tissue (usually embryonic tissue such as fetal or pre-fetal tissue), which stem cells have the characteristic of being capable under appropriate conditions of producing progeny of different cell types that are derivatives of all of the 3 germinal layers (endoderm, mesoderm, and ectoderm). These cell types may be provided in the form of an established cell line, or they may be obtained directly from primary embryonic tissue and used immediately for differentiation. Included are cells listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital- Seoul National University); HSF-1, HSF-6 (University of California at San Francisco); and H1, H7, H9, H13, H14 (Wisconsin Alumni Research Foundation (WCell Research Institute)).

Stem cells of interest also include embryonic cells of various types, exemplified by human embryonic stem (hES) cells, described by Thomson et al. (1998) Science 282:1145; embryonic stem cells from other primates, such as Rhesus stem cells (Thomson et al. (1995) Proc. Natl. Acad. Sci USA 92:7844); marmoset stem cells (Thomson et al. (1996) Biol. Reprod. 55:254); and human embryonic germ (hEG) cells (Shamblott et al., Proc. Natl. Acad. Sci. USA 95:13726, 1998). Also of interest are lineage committed stem cells, such as mesodermal stem cells and other early cardiogenic cells (see Reyes et al. (2001) Blood 98:2615-2625; Eisenberg & Bader (1996) Circ Res. 78(2):205-16; etc.) The stem cells may be obtained from any mammalian species, e.g. human, equine, bovine, porcine, canine, feline, rodent, e.g. mice, rats, hamster, primate, etc.

ES cells are considered to be undifferentiated when they have not committed to a specific differentiation lineage. Such cells display morphological characteristics that distinguish them from differentiated cells of embryo or adult origin. Undifferentiated ES cells are easily recognized by those skilled in the art, and typically appear in the two dimensions of a microscopic view in colonies of cells with high nuclear/cytoplasmic ratios and prominent nucleoli. Undifferentiated ES cells express genes that may be used as markers to detect the presence of undifferentiated cells, and whose polypeptide products may be used as markers for negative selection. For example, see US 2003/0224411 A1; Bhattacharya (2004) Blood 103(8):2956-64; and Thomson (1998), supra., each herein incorporated by reference. Human ES cell lines express cell surface markers that characterize undifferentiated nonhuman primate ES and human EC cells, including stage-specific embryonic antigen (SSEA)-3, SSEA-4, TRA-I-60, TRA-1-81, and alkaline phosphatase. The globo-series glycolipid GL7, which carries the SSEA-4 epitope, is formed by the addition of sialic acid to the globo-series glycolipid Gb5, which carries the SSEA-3 epitope. Thus, GL7 reacts with antibodies to both SSEA-3 and SSEA-4. The undifferentiated human ES cell lines did not stain for SSEA-1, but differentiated cells stained strongly for SSEA-I. Methods for proliferating hES cells in the undifferentiated form are described in WO 99/20741, WO 01/51616, and WO 03/020920.

Culture conditions of interest provide an environment permissive for differentiation, in which stem cells will proliferate, differentiate, or mature in vitro. Such conditions may also be referred to as differentiative conditions. Features of the environment include the medium in which the cells are cultured, any growth factors or differentiation-inducing factors that may be present, and a supporting structure (such as a substrate on a solid surface) if present. Differentiation may be initiated by formation of embryoid bodies (EB), or similar structures. For example, EB can result from overgrowth of a donor cell culture, or by culturing ES cells in suspension in culture vessels having a substrate with low adhesion properties.

The term "multi-lineage differentiation markers" means differentiation markers characteristic of different cell-types. These differentiation markers can be detected by using an affinity reagent, e.g. antibody specific to the marker, by using chemicals that specifically stain a cell type, etc as known in the art. Non-limiting examples of terminal differentiation markers include chromogranin A, NeuroD– enteroendocrine cells; mucin– goblet cells; villin, CD10- enterocytes, Lysozyme, Ang4– Paneth cells. Commmon progenitors for enteroendocrine, goblet and Paneth cells are detected by using an antibody against Math1. P-PTEN, SFRP5 and Musashil are specifically expressed in intestinal stem cells and intestinal progenitor cells. Intestinal alkaline phosphatase (IAP) marks enterocytes.

The term "candidate cells" refers to any type of cell that can be placed in co-culture with intestinal epithelial cells described herein. Candidate cells include without limitations, mixed cell populations, ES cells and progeny thereof, e.g. embryoid bodies, embryoid-like bodies, embryonic germ cells.

The term "candidate agents" means oligonucleotides, polynucleotides, siRNA, shRNA genes, gene products, small molecules and pharmacological compounds that is introduced in the intestinal cell culture described herein to assay for their effect on the explants.

The term "contacting" refers to the placing either candidate cells or candidate agents in the explant culture of mammalian intestinal cells. Contacting also encompasses co-culture of candidate cells with intestinal explants for at least 1 hour, or more than 2 hrs or more than 4 hrs in culture medium prior to placing them in a semi-permeable substrate. Alternatively, contacting refers to placing via trans-luminal injection, candidate cells into the lumen of explants growing as cysts.

"Screening" refers to the process of either co-culturing candidate cells with or adding candidate agents to the intestinal culture described herein. The effect of the candidate cells or candidate agents on intestinal culture is assessed by an increase in growth of the intestinal explants over basal levels and by presence of multilineage differentiation markers indicative of intestinal stem cells. The effect of candidate cells or candidate agents on the intestinal explant can be further evaluated by assaying the intestinal explant for long-term reconstitutive activity by serial in vitro passage, as well as by in vivo transplantation by subcutaneous implant assay and renal capsule assay.

"Ultrastructure" refers to the three-dimensional structure of intestinal epithelium observed in vivo. Ultrastructure includes the polarity of the intestinal epithelial cells and the morphology observed in the intestinal epithelium such as the presence of crypt and villus structures.

"R-spondin1" protein is described in Genbank Accession NP_001033722. R-spondin1(R-spo1) is one of the four proteins in the R-spondin protein family (Four human paralogs of R-spondin include R-spondin1-4).R-spo1 is a secreted glycoprotein containing a leading signal peptide, two cysteine-rich, furin-like domains, and one thrombospondin type 1 domain. R-Spo1 has no homology with Wnts, but synergizes with Wnts to activate β-catenin-dependent signaling.

Gel substrate, as used herein has the conventional meaning of a semi-solid extracellular matrix. Gel described here in includes without limitations, collagen gel, matrigel, extracellular matrix proteins, fibronectin, collagen in various combinations with one or more of laminin, entactin (nidogen), fibronectin, and heparin sulfate; human placental extracellular matrix.

An "air-liquid interface" is the interface to which the intestinal cells are exposed to in the cultures described herein. The intestinal tissue is may be mixed with a gel solution which is then poured over a layer of gel formed in container with a lower semi-permeable support, e.g. a membrane. This container is placed in an outer container that contains the medium such that the gel containing the tissue in not submerged in the medium. The intestinal cells are exposed to air from the top and to liquid medium from the bottom (FIG. 1).

By "container" is meant a glass, plastic, or metal vessel that can provide an aseptic environment for culturing cells.

Dibenzazepine (DBZ) is a cell-permeable compound that acts as a potent γ-secretase inhibitor and significantly lowers both brain and plasma A1340 levels by ~72% in Tg2576 mutant APP transgenic mouse model (100 µmol/kg, b.i.d). DBZ potently inhibits Notch processing ($IC_{50}$=1.7 nM in SupT1 cells) and induces conversion of proliferative crypt cells to post-mitotic goblet cells in both the C57BL/6 and ApcMin mouse models (10 µmol/kg, i.p).

Crohn's disease (also known as regional enteritis) is a chronic, episodic, inflammatory bowel disease (IBD) that affects the entire wall of the bowel or intestines. Crohn's disease can affect any part of the gastrointestinal tract from mouth to anus; as a result, the symptoms of Crohn's disease vary among afflicted individuals. The disease is characterized by areas of inflammation with areas of normal lining between in a symptom known as skip lesions. The main gastrointestinal symptoms are abdominal pain, diarrhea (which may be bloody or the blood may not be seen by the naked eye), constipation, vomiting, weight loss or weight gain. Crohn's disease can also cause complications outside of the gastrointestinal tract such as skin rashes, arthritis, and inflammation of the eye.

Colon cancer. The term "transformed" as used herein, refers to the process by which normal cells become tumorigenic, i.e. cancer cells. Colorectal cancer (CRC) is very common in Western countries. Incidence begins to rise at age 40 and peaks at age 60 to 75. 95% are adenocarcinomas. CRC most often occurs as transformation within adenomatous polyps. Serrated adenomas are particularly aggressive in their malignant transformation. About 80% of cases are sporadic, and 20% have an inheritable component. Predisposing factors include chronic ulcerative colitis and granulomatous colitis; the risk of cancer increases with the duration of these disorders. Elevated serum carcinoembryonic antigen (CEA) levels are present in 70% of patients with CRC, but this test is not specific and therefore is not recommended for screening. However, if CEA is high pre-operatively and low after removal of a colon tumor, monitoring CEA may help to detect recurrence earlier. CA 199 and CA 125 are other tumor markers that may be similarly used.

Patients with one of several known mutations have a 70 to 80% lifetime risk of developing CRC, including familial adenomatous polyposis (FAP), which correlates with mutations in the APC gene. Hereditary nonpolyposis colorectal carcinoma (HNPCC) is an autosomal dominant disorder responsible for 3 to 5% of cases of colorectal cancer (CRC). Symptoms, initial diagnosis, and treatment are similar to other forms of CRC. HNPCC is suspected by history and is confirmed by genetic testing.

DESCRIPTION OF THE SPECIFIC EMBODIMENTS

A culture system for long term culture of mammalian intestinal epithelium is provided for screening of candidate cells for presence of intestinal stem cells. In another embodiment of the invention, intestinal cell culture is used for screening agents for their effect on intestinal stem cells.

The cultured cells may be experimentally modified. In some embodiments, the intestinal explant cells are modified by exposure to viral or bacterial pathogens. In other embodiments the cells are modified by altering patterns of gene expression, e.g. by providing reprogramming factors to induce pluripotency or otherwise alter differentiation potential; or by introducing factors that provide for transformation of intestinal cells into carcinomas, e.g. APC; Kras; p53; etc. The experimentally modified cells are useful for investigation of the effects of therapeutic agents for anti-viral or anti-bacterial activity; for tumor therapy, for effects on differentiation, and the like. For example, the effect of a gain or loss of gene activity on the ability of cells to form an explant culture may be determined, or on the ability to undergo tumor transformation. The cytotoxicity of agents on primary intestinal epithelia, or on oncogenically transformed epithelial cultures may also be determined.

Inflammatory bowel diseases (IBD), colon cancer, mesenteric ischemia, congenital syndromes and trauma can produce functional loss or mandate physical resection of large sections of intestine extensive enough to compromise organ physiology. The ability to grow explants of intestinal tissue to be placed back into such patients is a valuable treatment option. Ability to screen for candidate cells for presence of intestinal stem cells is useful in therapies involving placing cells identified from this screen into explant culture derived from the intestinal tissue of a patient. Such cells can augment the ex vivo expansion of intestine, providing an autologous source of intestinal tissue and/or intestinal stem cells analogous to pancreatic islet transplantation. Development of ex vivo intestinal differentiation methodology would greatly facilitate tissue engineering or stem cell approaches to intestinal disorders, as opposed to currently available supportive measures such as total parenteral nutrition, in which all nutrition is supplied intravenously, or frank allogenic intestinal transplantation.

The ability to proliferate intestinal explants in vitro is valuable for development of therapies for treating intestinal diseases and trauma induced intestinal failure. These methods can also be used to regenerate intestinal tissue from patients. Intestinal tissue obtained from a patient by biopsy during endoscopy can be proliferated and expanded before being placed back into the patient to provide for faster regeneration of their intestinal tissue.

Culture, Proliferation and Expansion of Intestinal Epithelium

Figure 3:
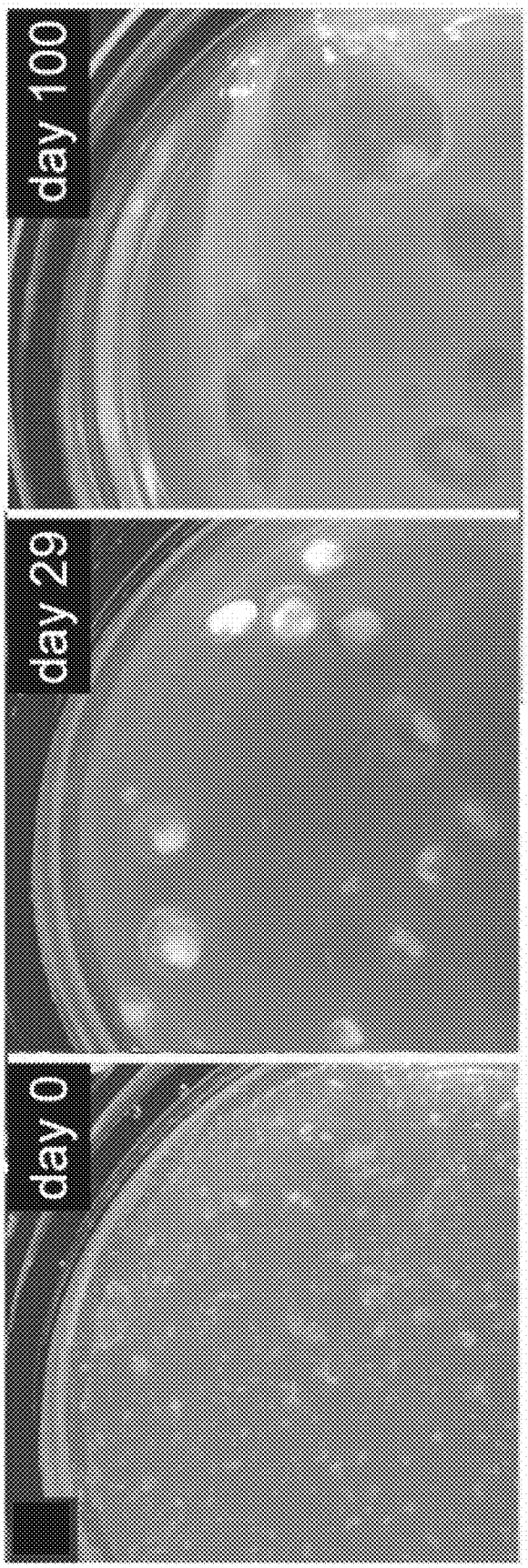
FIG. 3. Long term culture of intestinal tissue. Visualization of colonic explants from a neonatal mouse reveals continuous expansion over >100 days. Cysts increase in size from day 0, to day 29, to day 100.
Figure 4:
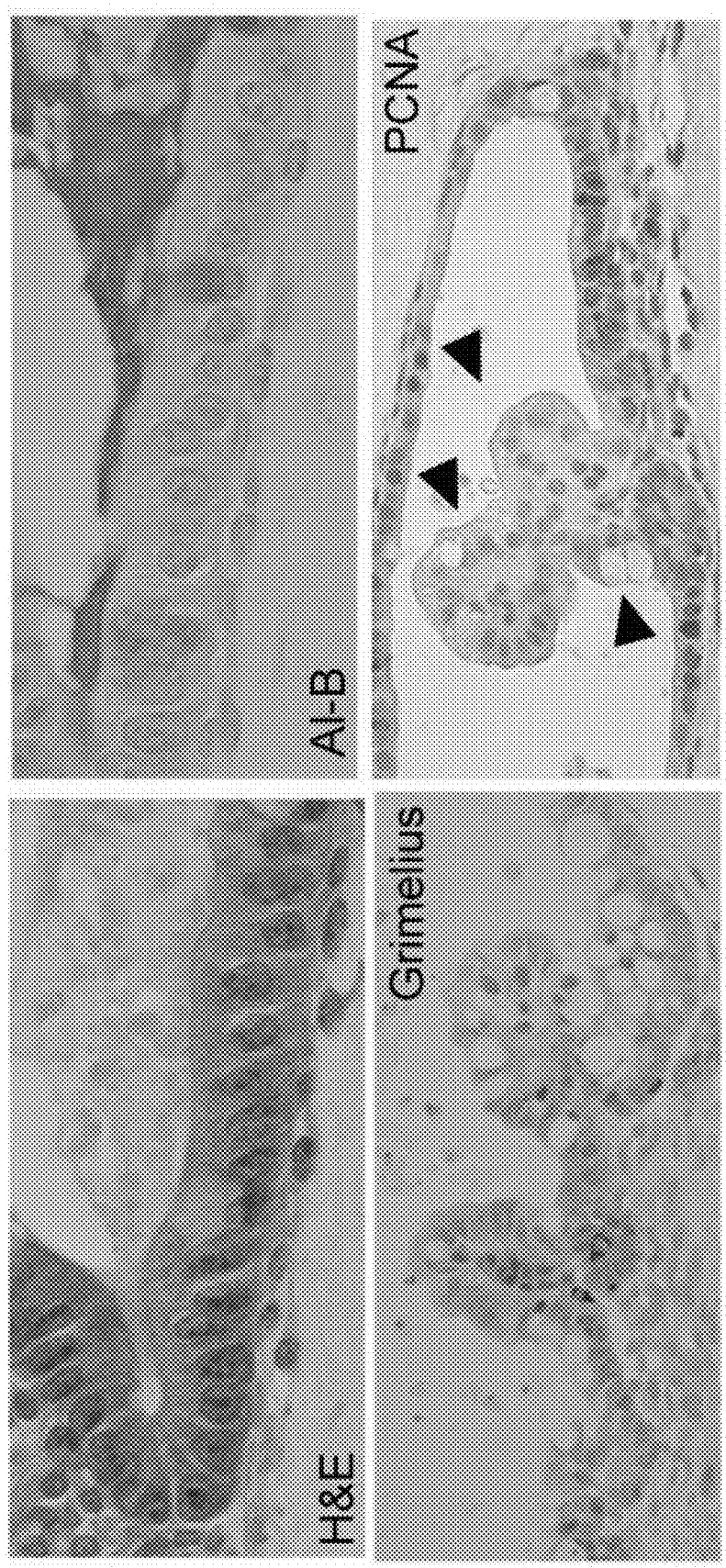
FIG. 4A-4D. Histological analysis of cultured jejunal mucosa (day 10).
Figure 5C:
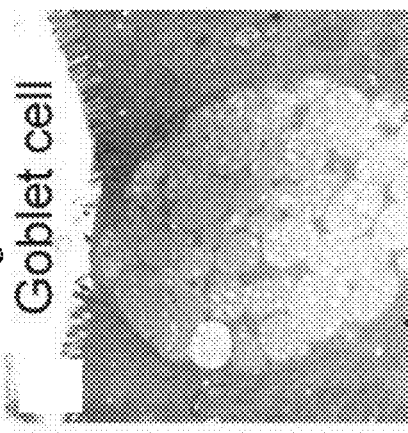
FIG. 5A-5E. Ultrastructure of intestinal explant cultures.
Figure 5E:
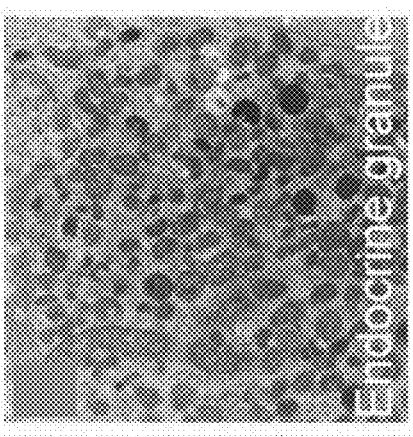
Figure 5B:
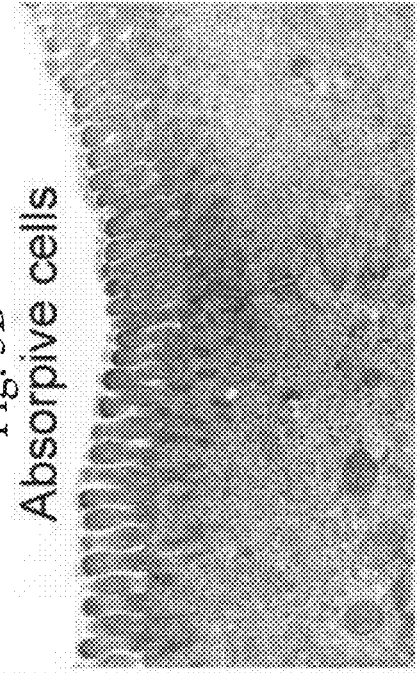
Figure 5D:
Figure 5A:
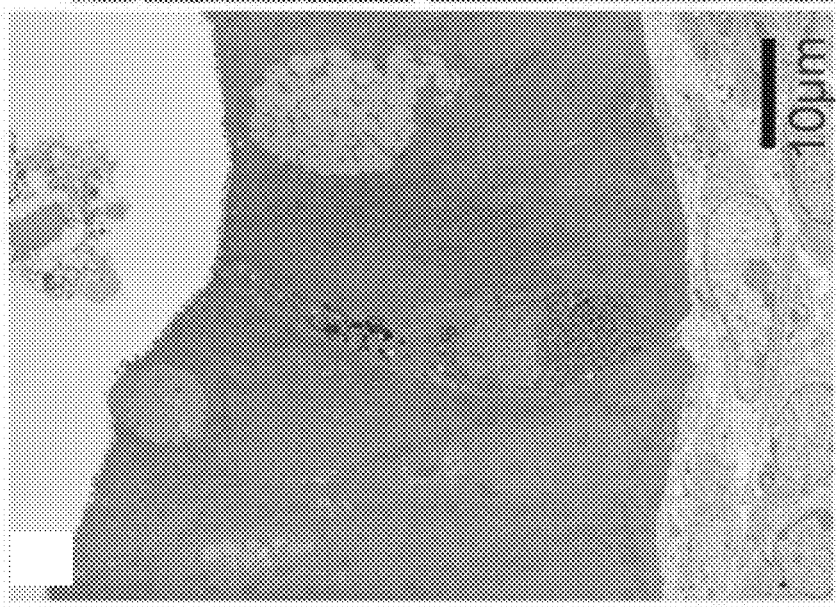

The culture system described herein provides for long term culture, proliferation and expansion of intestinal epithelial cells. Long term expansion encompasses growth of intestinal epithelium for more than 10 days, more than 30 days, more than 60 days, more than 100 days more than 150 days. Previously described culture methods allow culture of intestinal cells for less than 10 days. Intestinal tissue is cultured in a gel with an air-liquid interface (FIG. 1). Intestinal explants cultured by this method form hollow cysts (FIG. 2A-2C). The growth of these intestinal cysts can be followed visually to track their size. These cysts continue to grow over a period of about 150 days (FIG. 3). In addition to long-term proliferation, these intestinal explant cultures exhibit proper cellular ultrastructure, multi-lineage differentiation and Wnt-signaling.

Intestinal tissue is obtained surgically from the small or large intestine. Human intestinal tissue may be obtained by biopsy during endoscopy. Typically, pieces of intestine are minced to a size less than about 1 $mm^3$, and may be less than about 0.5 $mm^3$, or less than about 0.1 $mm^3$. The minced tissue is mixed with a gel solution. Subsequently, the tissue containing gel solution is layered over a layer of gel in a container with a lower semi-permeable support, e.g. a membrane. This container is placed into an outer container containing a suitable medium, for example HAMs F-12 medium with FCS at a concentration of from about 1 to about 25%, usually from about 5 to about 20%, etc. This arrangement allows nutrients to travel from the bottom, through the membrane and the gel layer to the gel layer containing the intestinal tissue. The level of the medium is maintained such that the top part of the gel layer containing the explants is not submerged in liquid but is exposed to air. Thus the intestinal tissue is grown in a gel with an air-liquid interface (FIG. 1).

In addition to long-term proliferation, these intestinal explant cultures exhibit proper cellular ultrastructure and multi-lineage differentiation. The ultrastructure of the intestinal explants in culture can be determined by performing Hematoxylin-eosin staining, PCNA staining (FIG. 4A-4D), electron microscopy (FIGS. 5A-5E), and the like using methods known in the art. Multi-lineage differentiation can be determined by performing labeling with antibodies to terminal differentiation markers, including, without limitation, chromogranin A, NeuroD$^-$ enteroendocrine cells; mucin$^-$ goblet cells; villin, CD10-absorptive epithelium/brush border, etc. Math1 immunofluorescence may be used detect the common progenitors for enteroendocrine and goblet cells. Alternatively, P-PTEN, SFRP5 and Mushashi immunofluorescence may be used detect putative crypt stem cell and progenitor population. The antibodies to detect these markers are commercially available from a number of sources.

Figure 7A:
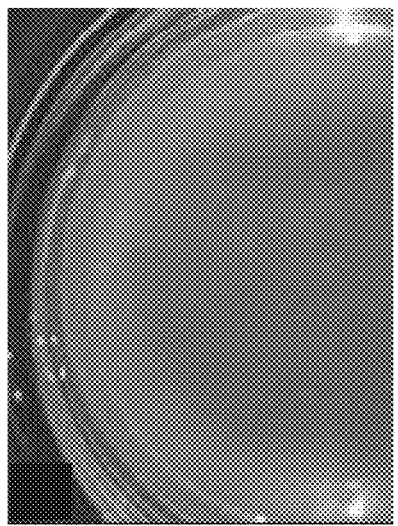
FIG. 7A-7C. The effect of Wnt agonist R-Spondin1 and Wnt inhibitor Dkk1 on intestinal explants (culture day 28).
Figure 7B:
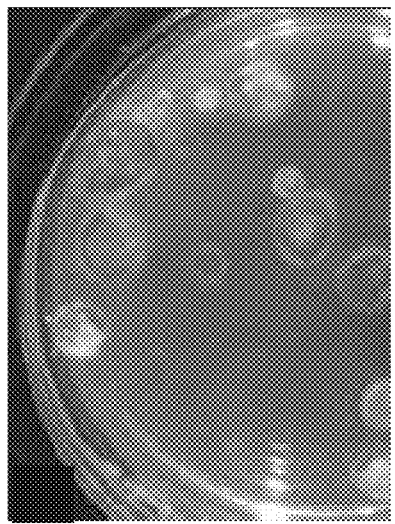
Figure 7C:
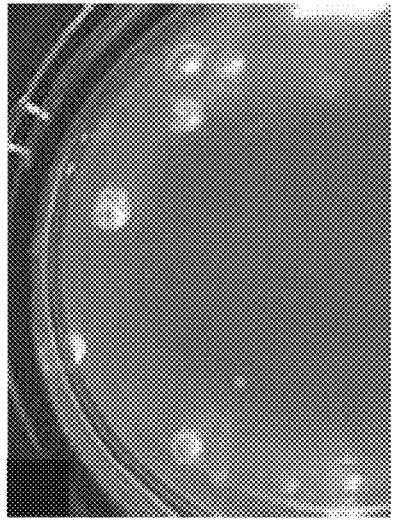

In one embodiment of the invention, a method of stimulating the growth of the above-described intestinal-explants by introducing R-spondin into the culture medium is provided. The intestinal explants cultured by above-described method exhibit normal Wnt-signaling and are responsive to proteins that either stimulate or inhibit intestinal growth. Exposure of the cultured intestinal epithelium to Wnt antagonists such as Dickkopf-1 (Dkk1) and Frizzled-8 ectodomain (Fz8-Fc) results in strong inhibition of explant growth (FIG. 7A-7C). R-spondin1 (Rspo1) is a secreted glycoprotein with no homology with Wnt, but which synergizes with Wnt to activate β-catenin dependent signaling (Kim et al., 2005, Kim et al., 2006). Intestinal cell culture exposed to RSpo1 exhibit increased growth (FIG. 7A-7C). The factors may be added to the culture at a concentration of at least about 500 ng/ml, at least about 0.5 µg/ml, at least about 50 µg/ml and not more than about 1 mg/ml, with change of medium every 1-2 days.

Screening Methods

Candidate agents are screened for their effect on intestinal cells in the cultures of the invention. Intestinal cells of interest include experimentally modified cells as described herein, including cancer cells, infected cells, cells treated with potentially cytotoxic agents and the like. Also included are intestinal stem cells, cancer stem cells, intestinal progenitors or differentiated or oncogenically transformed progeny thereof. The effect of an agent is determined by adding the agents to the intestinal cell cultures described above, usually in conjunction with a control intestinal cell culture lacking the agent. The growth of the intestinal tissue may be analyzed visually. The change in growth, differentiation, gene expression, proteome, phenotype with respect to markers, transport of agents, etc. in response to the agent is measured and evaluated by comparison to control intestinal cell culture. Agents of interest for analysis include any biologically active molecule with the capability of modulating, directly or indirectly, the growth rate of the intestinal explants, for example genetic agents, monoclonal antibodies, protein factors, small molecule therapeutics, chemotherapeutics, radiation, anti-sense RNA, RNAi, and the like.

In some embodiments, the intestinal explant culture is infected with an intestinal pathogen (bacterial or viral). Candidate agents are screened for anti-bacterial or anti-viral activity. Anti-bacterial or anti-viral activity of an agent can be assessed by monitoring growth, ultrastructure and viability of the explants. In other embodiments, the intestinal explant culture includes colon cancer cells, including cells suspected of being cancer stem cells.

Candidate agents possessing Notch/γ-secretase inhibitor activity may be detected by the increased conversion of the intestinal epithelial cells into goblet cells.

In a certain application of the culture system, the intestinal cell culture system is used to assess whether certain agents cause intestinal toxicity. In these applications, the intestinal culture is exposed to the candidate agent or the vehicle and its growth and viability is assessed. In these applications, analysis of the ultrastructure of the intestinal explants is also useful.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow-through method. Alternatively, the agents can be injected into the lumen of the intestinal cysts and their effect compared to injection of controls.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the growth rate.

The effect of a candidate agent on intestinal stem cells is assessed by comparing growth of intestinal explants in response to the agent is to that of control intestinal cell culture. In addition to analyzing the growth rate, the ultrastructure, the presence of differentiation markers can be determined to ascertain a normal intestinal tissue.

A wide variety of transporters are found in the intestine, and are involved in the membrane transport of daily nutrients as well as drugs. These intestinal transporters are located in the brush border membrane as well as basolateral membrane. Each transporter exhibits its own substrate specificity, and some have broader specificities than others. In addition, the distribution and characteristics of the intestinal transporters exhibit regional differences along the intestine, implying diverse physiologic functions and in some cases pathologic responses. Indeed several genetic disorders have been shown to result from deficient intestinal transporters. The development of prodrugs that target to intestinal transporters has been successful in improving oral absorption. For example, the intestinal peptide transporter is utilized in order to increase the bioavailability of several classes of peptidomimetic drugs, especially ACE inhibitors and beta-lactam antibiotics. The bioavailability of poorly absorbed drugs can be improved by utilization of the transporters responsible for the intestinal absorption of various solutes and/or by inhibiting the transporter involved in the efflux system. Recent advances in gene cloning and molecular biology techniques make it possible to study the characteristics and distribution of transporters at the molecular level. Based on molecular characterizations of membrane transporters and accumulated biochemical data on their specificities and kinetics, structural modification and targeting of a specific transporter is a promising strategy for the design of drugs that improve bioavailability and tissue distribution. The intestinal explant culture system offers a valuable tool that is useful in screens for agents that modulate intestinal transporters.

This culture system also offers a model system for testing candidate agents for uptake and absorption by the intestinal cells. Effective drug therapy relies on the interplay between the pharmacokinetics and pharmacodynamics (PK/PD) of the agent upon administration. During the initial stages of drug discovery, numerous studies are performed to assess the pharmacological effectiveness of new chemical entities (NCEs) to select a lead compound(s) that offers the greatest promise for therapeutic efficacy. While the ability of a drug to bind to a therapeutic target is critical to its clinical success, the ultimate effectiveness is also a function of its ability to reach the therapeutic target in sufficient concentrations to mitigate or treat the ailment. Therefore, the pharmacokinetics of any NCE must also be evaluated early in the drug discovery stages to enhance the rational selection of a lead compound from the many NCEs that are screened, based on not only biological activity but also potential in vivo bioavailability. Bioavailability is defined by the US FDA as "the rate and extent to which the active ingredient or active moiety is absorbed from a drug product and becomes available at the site of action" (21 CFR 320.1(a)). The overall bioavailability is largely determined by the absorption, distribution, metabolism, and excretion of selected compounds in targeted patient populations. Absorption across intestinal epithelium is especially important. The subject cell cultures offer a unique tool for measuring absorption rates of candidate agents. Similarly, cultures of the subject application are useful for screening for agents that modulate digestive enzymes.

Candidate Agents

Candidate agents of interest are biologically active agents that encompass numerous chemical classes, organic molecules, which may include organometallic molecules, inorganic molecules, genetic sequences, etc. An important aspect of the invention is to evaluate candidate drugs, select therapeutic antibodies and protein-based therapeutics, for their effect on intestinal stem cells. Candidate agents comprise functional groups necessary for structural interaction with proteins, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof. Included are pharmacologically active drugs, genetically active molecules, etc. Compounds of interest include chemotherapeutic agents, anti-inflammatory agents, hormones or hormone antagonists, ion channel modifiers, and neuroactive agents.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Candidate agent can also be polynucleotides and analogs thereof, which are tested in the screening assays of the invention by addition of the genetic agent to the intestinal cell culture. The introduction of the genetic agent can result in an alteration of the total genetic composition of the cell. Genetic agents such as DNA can result in an experimentally introduced change in the genome of a cell, generally through the integration of the sequence into a chromosome. Genetic changes can also be transient, where the exogenous sequence is not integrated but is maintained as episomal agents. Genetic agents, such as antisense oligonucleotides, can also affect the expression of proteins without changing the cell's genotype, by interfering with the transcription or translation of mRNA. Genetic agents, such as short interfering RNA (siRNA) or short hairpin (shRNA), can effect expression of proteins without changing the cell's genotype by mediated the degradation of the mRNA it binds to. The effect of a genetic agent is to increase or decrease expression of one or more gene products in the cell.

Introduction of an expression vector encoding a polypeptide can be used to express the encoded product in cells lacking the sequence, or to over-express the product. Various promoters can be used that are constitutive or subject to external regulation, where in the latter situation, one can turn on or off the transcription of a gene. These coding sequences may include full-length cDNA or genomic clones, fragments derived therefrom, or chimeras that combine a naturally occurring sequence with functional or structural domains of other coding sequences. Alternatively, the introduced sequence may encode an anti-sense sequence; be an antisense oligonucleotide; siRNA or a shRNA, encode a dominant negative mutation, or dominant or constitutively active mutations of native sequences; altered regulatory sequences, etc. Instead of being expressed from a vector transfected or transduced into the intestinal epithelial cells, the oligonucleotides, siRNA or shRNA can be directly transfected or transduced into the intestinal cells.

In addition to sequences derived from the host cell species, other sequences of interest include, for example, genetic sequences of pathogens, for example coding regions of viral, bacterial and protozoan genes, particularly where the genes affect the function of human or other host cells. Sequences from other species may also be introduced, where there may or may not be a corresponding homologous sequence.

A large number of public resources are available as a source of genetic sequences, e.g. for human, other mammalian, and human pathogen sequences. A substantial portion of the human genome is sequenced, and can be accessed through public databases such as Genbank. Resources include the uni-gene set, as well as genomic sequences. For example, see Dunham et al. (1999) Nature 402, 489-495; or Deloukas et al. (1998) Science 282, 744-746.

cDNA clones corresponding to many human gene sequences are available from the IMAGE consortium. The international IMAGE Consortium laboratories develop and array cDNA clones for worldwide use. The clones are commercially available, for example from Genome Systems, Inc., St. Louis, Mo. Methods for cloning sequences by PCR based on DNA sequence information are also known in the art.

Methods that are well known to those skilled in the art can be used to construct expression vectors containing coding sequences and appropriate transcriptional and translational control signals for increased expression of an exogenous gene introduced into a cell. These methods include, for example, in vitro recombinant DNA techniques, synthetic techniques, and in vivo genetic recombination. Alternatively, RNA capable of encoding gene product sequences may be chemically synthesized using, for example, synthesizers. See, for example, the techniques described in "Oligonucleotide Synthesis", 1984, Gait, M. J. ed., IRL Press, Oxford.

A variety of host-expression vector systems may be utilized to express a genetic coding sequence. Expression constructs may contain promoters derived from the genome of mammalian cells, e.g., metallothionein promoter, elongation factor promoter, actin promoter, etc., from mammalian viruses, e.g., the adenovirus late promoter; the vaccinia virus 7.5K promoter, SV40 late promoter, cytomegalovirus, etc.

In mammalian host cells, a number of viral-based expression systems may be utilized, e.g. retrovirus, lentivirus, adenovirus, herpesvirus, and the like. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the gene product in infected hosts (see Logan & Shenk, 1984, Proc. Natl. Acad. Sci. USA 81:3655-3659). Specific initiation signals may also be required for efficient translation of inserted gene product coding sequences. These signals include the ATG initiation codon and adjacent sequences. Standard systems for generating adenoviral vectors for expression on inserted sequences are available from commercial sources, for example the Adeno-X™ expression system from Clontech (Clontechniques, January 2000, p. 10-12).

In cases where an entire gene, including its own initiation codon and adjacent sequences, is inserted into the appropriate expression vector, no additional translational control signals may be needed. However, in cases where only a portion of the gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516-544).

In a preferred embodiment, methods are used that achieve a high efficiency of transfection, and therefore circumvent the need for using selectable markers. These may include adenovirus infection (see, for example Wrighton, 1996, J. Exp. Med. 183: 1013; Soares, J. Immunol., 1998, 161: 4572; Spiecker, 2000, J. Immunol 164: 3316; and Weber, 1999, Blood 93: 3685); and lentivirus infection (for example, International Patent Application WO000600; or WO9851810). Adenovirus-mediated gene transduction of endothelial cells has been reported with 100% efficiency. Retroviral vectors also can have a high efficiency of infection with endothelial cells, provides virtually 100% report a 40-77% efficiency. Other vectors of interest include lentiviral vectors, for examples, see Barry et al. (2000) Hum Gene Ther 11(2):323-32; and Wang et al. (2000) Gene Ther 7(3):196-200.

For the purpose of analysis of the effect of gene overexpression introduction of the test gene into a majority of cells (>50%) in a culture is sufficient. This can be achieved using viral vectors, including retroviral vectors (e.g. derived from MoMLV, MSCV, SFFV, MPSV, SNV etc), lentiviral vectors (e.g. derived from HIV-1, HIV-2, SIV, BIV, FIV etc.), adeno-associated virus (AAV) vectors, adenoviral vectors (e.g. derived from Ad5 virus), SV40-based vectors, Herpes Simplex Virus (HSV)-based vectors etc. A preferred vector construct will coordinately express a test gene and a marker gene such that expression of the marker gene can be used as an indicator for the expression of the test gene, as well as for analysis of gene transfer efficiency. This can be achieved by linking the test and a marker gene with an internal ribosomal entry site (IRES) sequence and expressing both genes from a single bi-cistronic mRNA. IRES sequence could be from a virus (e.g. EMCV, FMDV etc) or a cellular gene (e.g. eIF4G, BiP, Kv1.4 etc). The examples of marker genes include drug resistance genes (neo, dhfr, hprt, gpt, bleo, puro etc) enzymes (ß-galactosidase, alkaline phosphatase etc) fluorescent genes (e.g. GFP, RFP, BFP, YFP) or surface markers (e.g. CD24, NGFr, Lyt-2 etc). A preferred marker gene is biologically inactive and can be detected by standard immunological methods. Alternatively, an "epitope tag" could be added to the test gene for detection of protein expression. Examples of such "epitope tags" are c-myc and FLAG (Stratagene). A preferred viral vector will have minimal or no biological effect on the biomap apart from the genetic agent being tested. An example of such viral vectors are retroviral vectors derived from the MoMLV or related retroviruses, as listed above. By gating on the population of genetically modified cells, the unmodified cells in the culture can be excluded from analysis, or can be compared directly with the genetically modified cells in the same assay combination. For example, see Bowman et al. (1998) J. Biol. Chem. 273:28040-28048.

Using Intestinal Explant Cultures to Screen for Agents Effective Against Intestinal Pathogens The subject cells are useful for in vitro assays and screening to detect agents that modulate effect of viral and bacterial pathogens. A wide variety of assays may be used for this purpose, including toxicology testing, immunoassays for protein binding; determination of cell growth, differentiation and functional activity; production of hormones; and the like.

In screening assays with biologically active pathogens, the subject cell culture is contacted with the agent of interest, for example in the presence of a pathogen, and the effect of the agent assessed by monitoring output parameters, such as expression of markers, cell viability, and the like. The cells may be freshly isolated, cultured, genetically altered as described above; or the like. The cells may be environmentally induced variants of clonal cultures: e.g. split into independent cultures and grown under distinct conditions, for example with or without pathogen; in the presence or absence of other cytokines or combinations thereof. The manner in which cells respond to an agent, particularly a pharmacologic agent, including the timing of responses, is an important reflection of the physiologic state of the cell.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

An important aspect of the invention is to evaluate candidate drugs, including toxicity testing, to test the effect of enteric viruses, e.g. rotavirus, calcivirus, astrovirus, enteric adenovirus etc., antiviral agents; to test the effect of enteropathic bacteria such as *Campylobacter* spp., *Salmonella* spp., *Shigella* spp., and *Escherichia coli* and the like; to screen anti-bacterial agents using cultures exposed to bacterial pathogens. Similarly, using cultures exposed to viral pathogens to screen for anti-viral agents.

Intestinal pathogens have been well studied and described (see for example, Microbial Pathogenesis and the Intestinal Epithelial Cell—Gail A. Hecht—2003—ASM press). Intestinal pathogens described in this book are hereby incorporated by reference.

Screening for Candidate Cells for Presence of Intestinal Stem Cells

In another embodiment of the invention the method of long-term culture of intestinal tissue is used to screen candidate cells for presence of intestinal stem cells or for presence of potential to develop into intestinal stem cells. Candidate cells are screened by adding the cells to the intestinal cell cultures described above, usually in conjunction with a control intestinal cell culture lacking the candidate cell. Intestinal stem cells divide continuously, renewing themselves and producing intestinal progenitor cells. Intestinal progenitor cells in turn give rise to four principal epithelial lineages: absorptive enterocytes, mucin secreting-goblet cells, peptide hormone secreting enteroendocrine cells, and Paneth cells. Thus all cells of the intestinal epithelium arise from the intestinal stem cells. The intestinal stem cells continuously renew themselves, fueling long term proliferation and reconstitution of intestinal epithelium. Thus the presence of intestinal stem cells among candidate cells can be assayed by increase in the growth of explants compared to basal levels, analysis of multi-lineage differentiation, and analysis of long term proliferation. Long-term growth, presence of normal cellular ultrastructure and recapitulation of Wnt-dependent signaling in the intestinal explants cultured by methods described above are indicative these cultures provide the environment necessary for the maintenance of intestinal stem cells. This method of culturing will provide the candidate cells with the proper environment permissive and instructive for adopting an intestinal stem cell fate. Candidate cells capable of adopting intestinal stem cell fate, when co-cultured with intestinal explant cultures will stimulate explant growth above basal levels.

Candidate cells can be detectably marked, for example via expression of a marker such as GFP or β-galactosidase. Candidate cells marked via expression of GFP are derived by standard techniques. GFP transduced candidate cells can be generated by techniques well known in the art, for example using a viral vector expressing GFP. Labeled candidate cells may be co-cultured with non-labeled intestinal explants. The candidate cells may be mixed with the explant culture prior to mixing with gel (and subsequent long term culture). Alternatively the candidate cells may be mixed with explants that have been grown to the cyst stage, and which are then injected into the lumen of the cyst. Cells may be introduced in a limiting dilution, or as a population, e.g. 1, 5, 10, 100, 500, 1000 or more cells per culture. The co-culture of candidate cells and explant may be culture for at least about 1, 2, 3, 4, 5, 6, 7, 8, 9, 10, 11, 12, or more weeks prior to evaluation for differentiation into epithelial cell lineages.

The assessment of the candidate cells may be performed by visual observation, e.g. the stimulation of growth of intestinal explants in culture compared to the explants not co-cultured with the candidate cells. Alternatively, expression of various differentiation markers can be valuated. Immunofluorescence can be performed using antibodies against intestinal differentiation markers, including, without limitation, chromogranin A, NeuroD– enteroendocrine cells; mucin– goblet cells; villin, CD10– absorptive epithelium/brush border, Lysozyme, Ang4-Paneth cells. Dual color immunofluorescence may be performed with the intrinsic GFP signal to confirm co-localization of differentiation markers with candidate cells.

Math1 immunfluorescence can be used to detect the common progenitors for enteroendocrine, goblet and Paneth cells; alternatively, P-PTEN, SFRP5 and Musashi1 immunfluorescence will detect putative crypt stem cells and progenitor cells. As above, co-localization may be performed with an intrinsic GFP signal of the candidate cells.

Differentiated cell types in the explant culture may also be analyzed via immuno-electron microscopy to confirm faithful recapitulation of intestinal epithelium cellular ultrastructure of candidate cell derived progenies.

Another criteria for stem cell function is self-renewal, with concomitant long-term proliferation and reconstitution activities. Long-term proliferation of GFP-transduced candidate cells within the explants can be assayed both in vitro and in vivo, and compared to control explants without the candidate cells.

Methods of in vitro analysis include, without limitation, serial passage of explant:candidate co-cultures. For example, cysts may be transplanted intact or subdivided as fragments into fresh gel followed by continued culture. Explants thus transplanted may eventually be harvested and sectioned for microscopic or visual analysis. Serial transplantability of explants co-cultured with candidate cells are compared to that of explants grown without candidate cells.

Methods of in vivo analysis include various methods where explants are transferred to an in vivo environment. In some embodiments, intestinal explants are cultured using the methods described above, extracted from the gel, and implanted under the renal capsule of an experimental animal, e.g. syngeneic or immunodeficient mice, then allowed to grow for a suitable period of time, e.g. at least about 1 week, at least about 2 weeks, at least about 3-4 weeks, at least about 1, 2, 3, 4 or more months, etc. For example, see FIG. 6. Alternative sites for implantation include subcutaneous implantation into a syngeneic or immunodeficient animal. This assay can be modified to utilize various marker systems, e.g. luciferase expressing cells that permit periodic non-invasive imaging after luciferin injection. Growth and serial transplantability is compared between explants with and without candidate cells.

Screening candidate cells for presence of intestinal stem cells or for cells capable of adopting intestinal stem cell fate has attendant therapeutic purpose. Human intestinal tissue explant can be regenerated at an accelerated rate in vitro upon co-culturing with such a cell. This allows faster turn around time for transplanting the explant back into a patient. Additionally such cells can be placed directly into the intestinal lumen of patients suffering from intestinal disease or trauma to enhance the in vivo regeneration of the intestine.

Screening and/or Expansion of Candidate Cancer Stem Cells; Oncogenes and Tumor Suppressors In another embodiment of the invention the method of long-term culture of intestinal tissue is used to screen for agents such as genes involved in cancer initiation and progression. In some embodiments the screening assays are directed at candidate cancer stem cells. This may be achieved with or without testing the presence of intestinal stem cells within the cancer stem cell population or the presence of potential to develop into intestinal stem cells. Candidate cancer stem cells are screened by adding the cells to the intestinal cell cultures described above, usually in conjunction with a control intestinal cell culture lacking the candidate cell, and detecting the presence of proliferating cancer stem cells, e.g. cells having markers or characteristics of the cancer stem cell. Thus the presence of cancer stem cells among candidate cells can be assayed by increase in the growth of explants compared to basal levels, and/or analysis of their multi-lineage differentiation, and/or analysis of long term proliferation.

Methods for purifying cancer stem cells have been previously described, for example in US20070292389A1 and US2070238127A1. US20070292389A1 describes purification of cancer stem cells from solid epithelial tumors. The method of purification and amplification of cancer stem cells disclosed in US20070292389A1 is herein incorporated by reference.

In other embodiments, non-transformed intestinal cells are experimentally modified prior, or during the culture period by altering patterns of gene expression by introducing factors (e.g. expressible coding sequences, anti-sense and RNAi agents, etc.) that provide for transformation of intestinal cells into carcinomas, e.g. APC; Kras; p53; etc. The experimentally modified cells are useful for investigation of the effects of therapeutic agents for tumor therapy and identification of new therapeutic molecular targets. Such methods allow investigation of cancer initiation and treatment. Agents of interest include, without limitation, chemotherapy, monoclonal antibodies or other protein-based agents, radiation/radiation sensitizers, cDNA, siRNA, shRNA, small molecules, and the like.

The following examples are put forth so as to provide those of ordinary skill in the art with a complete disclosure and description of how to make and use the subject invention, and are not intended to limit the scope of what is regarded as the invention.

EXPERIMENTAL

Example 1

Culture of Intestinal Explants

Provided herein is a tissue culture system for long-term culture of explants of murine small or large intestine. Explants cultured by this method exhibit long-term proliferation, multi-lineage differentiation, preservation of cellular ultrastructure and differentiation markers characteristic of absorptive enteroytes, goblet cells and enteroendocrine cells.

Small intestine or colon of C57Bl/6J mice is procured under sterile conditions, minced and mixed with type I collagen gel. Subsequently, these explant containing gels are poured onto transwell cell culture inserts with a collagen gel layer. Transwell cell culture inserts are available commercially from a number if resources e.g. Corning, Signaaldrich. These cell culture inserts are placed into secondary outer dishes containing HAMs F-12 with 20% FCS. Examples of cystic structures formed by this culture method and cultured for more than 100 days are shown in FIG. 3. Proliferation and histology of the explant is depicted in FIG. 4A-4D. Electron micrographs of the intestinal explants in FIG. 5A-5E reveal that the ultrastructure of the intestinal epithelium is preserved.

Methods

Preparation of Culture System.

Before preparing the tissue, an inner container with a gel as bottom layer was made. The procedure described herein used Cellmatrix type I-A (Nitta Gelatin Inc.) e.g. collagen gel. The inner dish has permeable membrane bottom. Millicell culture plate inserts (Millicell-CM, Millipore Co.) or Falcon cell culture inserts (BD Co.) was used as the inner dish. 1 ml of collagen gel solution was poured into a 30-mm diameter inner dish in combination with 60 mm diameter outer dish and 2 ml of culture media. 0.3 ml collagen gel solution was poured into 10-mm diameter inner dish in combination with a 24-well outer dish and 0.5 ml of culture media.

Preparation and Culture of Intestinal Tissue.

Small or large intestine was removed from mouse (fetus, neonate, juvenile, or adult) aseptically. The removed tissue was immediately immersed in ice-cold PBS or other culture media/tissue preservative solution such as Ham's F12, MEM, etc. The small intestine or colon are opened lengthwise and washed in ice-cold PBS to remove all luminal contents. The washed tissue was minced with scissors to a size less than about 0.1 mm³. The minced tissue was mixed in ice-cold collagen gel solution and poured onto the prepared inner dish. The inner dish was placed in an outer dish. The gel was solidified at 37° C. for 30 min. After solidification of the gel, culture media was poured into outer dish. Ham's F12 supplemented with 20% fetal calf serum and 50 µg/ml gentamicin was used as culture medium. The culture can be sustained for over a year at 37° C. in a humidified atmosphere of 5% $CO_2$ in air. Medium was changed about every 7 days.

Visualization of Intestinal Explants.

Live intestinal explant cultures were observed by phase-contrast microscopy or stereo microscopy. For histological analysis, culture assembly was fixed with 4% PFA and embedded in paraffin. Deparaffinized cross sections were stained with hematoxylin and eosin. Deparaffinized sections were also used for immunohistochemistry. For ultrastructural analysis by transmission electron microscopy, intestinal explants were fixed with 2.5% glutaraldehyde and 1% osmic acid, dehydrated with alcohol, and embedded in epoxy resin.

Example 2

Coculture of Human Embryonic Stem Cells with Intestinal Cell Culture

Screening of candidate cells for the presence of intestinal stem cells or for cells with ability to adopt intestinal stem cell fate is performed using human embryonic stem (hES) cells as candidate cells. The intestinal explants cultured by methods of example 1 reproduce the in vivo Wnt-dependency of intestinal proliferation (i.e. stimulation by RSpo1 and inhibition by Dkk1/Fz8-Fc), suggestive of accurate recapitulation of the intestinal stem cell (ISC) niche. Here we provide a method for screening for commitment of hES cells to intestinal stem cell fate. hES cells adapted to intestinal stem cell fate will stimulate the further proliferation and long term growth of the intestinal explants.

hES cells are marked with GFP expression using VSV-G pseudotyped lentivirus expressing GFP. VSV-G pseudotyped lentivirus expressing GFP in a self-inactivating (SIN) vector is generated by transient transfection of 293T cells with gagpol, VSV-G and rev helper plasmids followed by concentration by ultracentrifugation. Human ES H1 and H9 cells (WCell) are cultured on mouse embryonic fibroblasts (MEF) in DMEM-F12 with 20% KNOCKOUT serum replacement and 4 ng/ml human bFGF with daily medium changes, and weekly subcloning of mature colonies. Undifferentiated hES cells are infected with GFP lentivirus using 2×2 hr cycles of infection with 6 µg/ml polybrene, at MOI of 10. This has been reported to produce approximately 50% transduction efficiency of the H1 line. Following infection, GFP-transduced hES cells are cultured on MEF to confirm undifferentiated morphology.

Explant culture is performed as described in example 1. The GFP-transduced hES lines H1 and H9 maintained on MEF feeder layers (see above) are trypsinized to single cell suspensions and recombined with the intestinal explants by several methods. First, GFP-transduced hES cells or medium without hES cells are physically co-cultured with the naïve intestinal explants for 1, 2 and 4 hours in HAMs F-12 with 20% FCS prior to mixing with collagen gel and long-term culture. Second, explants are grown as cysts for 7, 14, 21 or 42 days to establish mature ISC niches, prior to intraluminal injection of 1, 10 or 100 GFP-transduced ES cells using a 26G needle directly into individual cysts or subepithelial microinjection under stereomicroscope guidance into the presumptive niche area. This establishes both an alternative methodology as well as potentially establishes the ability of single hES cells to exhibit long-term, clonal proliferation with multi-lineage intestinal differentiation (see below).

One parameter of stem cell function is the ability to undergo multi-lineage differentiation. Explant:hES cell co-culture is performed as described above for 14, 21, 42 or 84 days followed by frozen sectioning and compared to control explants without hES cells. Terminal differentiation markers are analyzed using antibodies specific to the different terminal markers. Immunofluorescence is performed using antibodies against intestinal differentiation markers (chromogranin A, NeuroD– enteroendocrine cells; mucin– goblet cells; villin, CD10-absorptive epithelium/brush border, Lysozyme, Ang4– Paneth cells) using Cy3-congugated secondaries; dual color immunofluorescence is performed with the intrinsic GFP signal to confirm co-localization of differentiation markers within the lentivirus-transduced hES-derived populations. Math1 immunofluorescence detects the common progenitors for enteroendocrine, goblet and Paneth cells; alternatively, P-PTEN, SFRP5 and Musashi1 IF can be used to detect putative crypt stem and progenitor populations. As above, co-localization with the intrinsic GFP signal of the lentivirus-transduced hES cells is performed. The differentiated cell types in explant culture are analyzed via immuno-electron microscopy using anti-GFP to confirm faithful recapitulation of cellular ultrastructure of hES cell-derived progeny.

One criteria for stem cell function is self-renewal, with concomitant long-term proliferation and reconstitution activities. Long-term proliferation of GFP-transduced intestinal stem cells within the explant niche is assayed both in vitro and in vivo, and compared to control explants without putative intestinal stem cells. In addition to long-term explant: intestinal stem cell co-culture (>84 days as culture permits), serial passage of explant: intestinal stem cell co-culture is performed. Cysts are enucleated from the collagen gel with scissors and transplanted intact or subdivided as fragments into fresh collagen gel followed by continued culture. This cycle is repeated every 42-84 days as allowed by continued viability. Explants are harvested and embedded in OCT, followed by dual color fluorescence analysis using anti-PCNA with Cy3-conjugated secondary and intrinsic GFP signal. Similarly, TUNEL staining is performed to detect apoptotic populations. Attention is paid to serial transplantability with or without intestinal stem cell co-culture. This can be similarly performed with embryonic stem cells instead of intestinal stem cells.

In vivo analysis of long-term reconstitution is done by performing renal capsule assay and subcutaneous implantation assay:

(1) Renal capsule assay. Intestinal explants from actin-GFP mice are cultured using above mentioned methods, extracted from the gel, and implanted under the renal capsule of naïve SCID mice, with growth in this ectopic location for 30 days (the longest time evaluated) (FIG. 6A-6C). This assay is modified to utilize actin-luciferase mice, permitting periodic non-invasive imaging after luciferin injection using the Xenogen cameras. Accordingly, actin-luciferase intestinal explants are co-cultured with GFP-transduced hES cells as described above. After 14, 21, 42 or 84 days, these cysts are transplanted under the renal capsule of SCID mice, to minimize rejection of the hES cell component. Following prolonged periods of explant growth in this ectopic kidney location as confirmed by sequential increases in luciferase signal, the grafts are retrieved at days 50, 100 and 200 post-transplantation by frozen sectioning of the recipient kidney, followed by analysis of the GFP-positive (i.e. hES cell-derived) progeny by dual-color IF using Cy3-labeled anti-differentiation marker and anti-PCNA antibodies as described above. Growth and serial transplantability is compared between explants with and without hES cells.

(2) Subcutaneous implantation assay. Freshly isolated crypts from mouse intestine have been described to be successfully implanted subcutaneously into syngeneic mice with growth as cysts (Booth et al., 1999; Slorach et al., 1999). As an alternative approach, actin-luciferase explant: GFP-hES co-cultures are retrieved at days 14, 21 and 42 followed by subcutaneous implantation into SCID mice, and periodic non-invasive Xenogen imaging. As above, grafts can be retrieved at days 50, 100 and 200 post-transplantation by frozen sectioning of the recipient kidney, followed by analysis of the GFP-positive progeny by dual-color IF using Cy3-labeled anti-differentiation marker and anti-PCNA antibodies as described above. Growth and serial transplantability is compared between explants with and without hES cells.

Example 3

Figure 10:
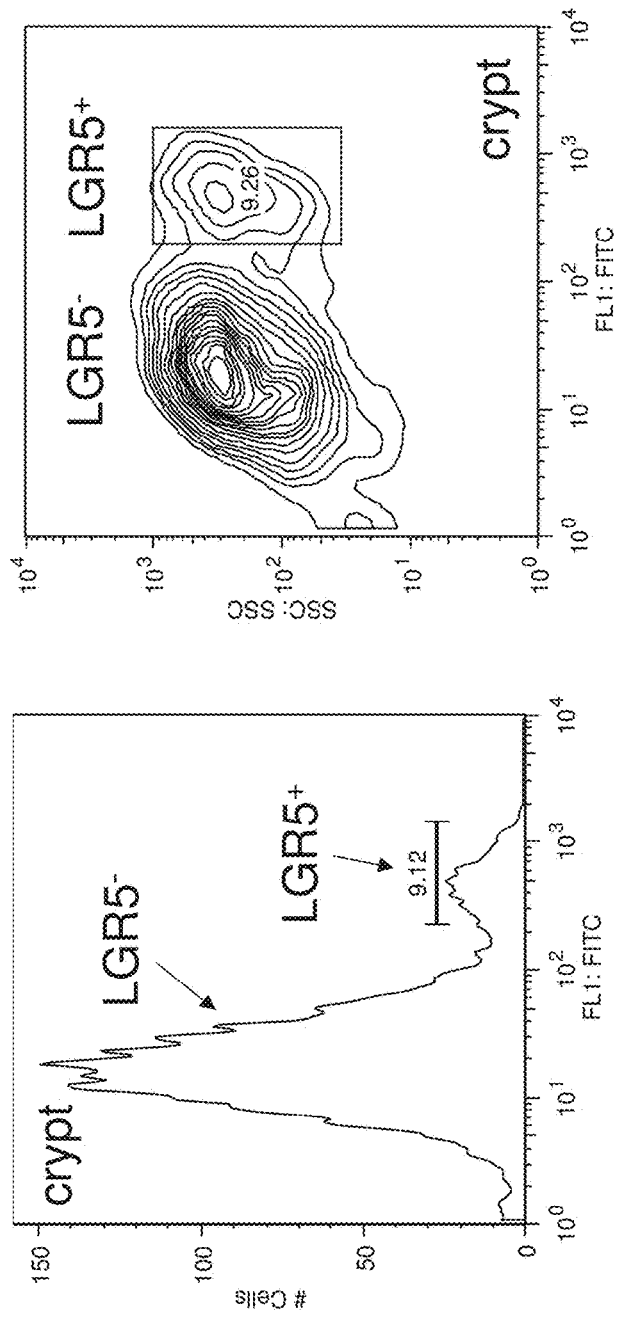
FIG. 10. Detection of the LGR5+ presumptive stem cell population in the crypt fraction of mouse small intestine. The crypt fraction of adult mouse small intestine was isolated by differential centrifugation, followed by enzymatic and mechanical disaggregation into single cells. The crypt cell suspension was stained with anti-LGR5, anti-CD45 (pan-hematopoietic marker) and propidium iodide (P1, stains dead cells). The CD45(−) PI(−) fraction of the crypt suspension was fractionated by FACS into LGR5 positive and negative fractions, with approximately 9% positivity for LGR5 amongst crypt epithelial cells. A histogram (left panel) and contour plot (right panel) are depicted indicating clear fractionation and the ability to cleanly resolve LGR5+ crypt cells from LGR5− populations.
Figure 11:
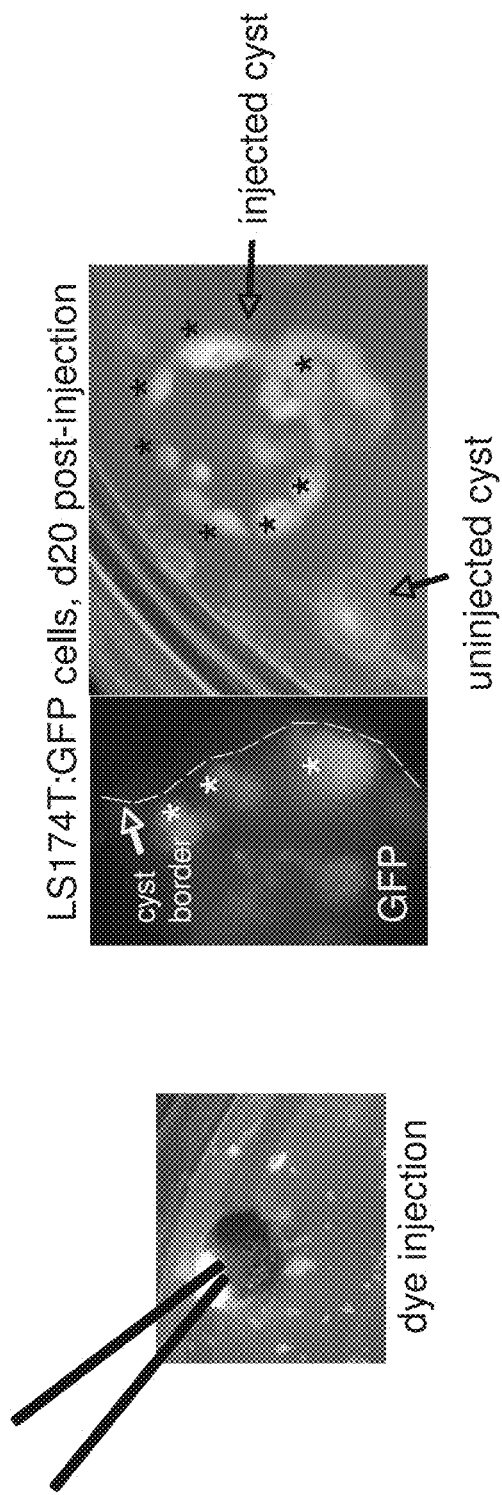
FIG. 11. Successful microinjection of LGR5$^+$ LS174T cells into colonic cyst cultures. We have devised methodology to successfully microinject LGR5$^+$ LS174T cells into colonic explant cultures. A sample dye injection is depicted at left. On right, 600 lentivirus GFP labeled LS174T cells were microinjected into a colon explant cyst. After 20 days of culture, obvious GFP expression and cell proliferation is seen (see *).

The GPCR LGR5 is a robust ISC marker. Rabbit anti-human LGR5 ectodomain antisera has been demonstrated to recognize both human and mouse LGR5 by FACS (FIG. 10). Notably, this anti-LGR5 antisera recognizes a subpopulation of cells from the crypt fraction of mouse small intestine (FIG. 10) corresponding to the LGR5$^+$ ISCs. LGR5$^+$ ISCs are introduced into the Wnt- and Notch-dependent niche recapitulated by our intestinal cultures. We have performed successful microinjection of human GFP-marked LGR5$^+$ LS174T cells into our intestinal cultures.

A. Isolation of LGR5+ Cells from Human Colon.

The rabbit anti-human LGR5 polyclonal antisera recognize both human and mouse LGR5$^+$ cells upon flow cytometry.

(i). Human LGR5+ Cell Isolation.

Normal human colon or human IBD colon obtained from surgery is subjected to collagenase A and DNaseI digestion followed by pipetting and passage through a cell strainer to generate a single cell suspension. The single cell suspensions is centrifuged and resuspended in PBS with 5% FBS, and enrichment performed prior to sorting by immunodepletion of hematopoietic and endothelial elements using anti-CD45 and anti-CD31 magnetic beads. Polyclonal anti-human LGR5 Ab (1:100; Hsueh lab) and APC-conjugated goat anti-rabbit IgG (1:1000) is used to stain LGR5$^+$ ISC at 4° C. LGR5 FACS is performed under sterile conditions on an Aria sorter (Stanford FACS Core) and analyzed by FlowJo (TreeStar). Viable single cells are gated by PI staining.

To perform lineage tracing of the human LGR5+ cells, in some downstream applications, the human LGR5+ ISCs is monitored with (1) anti-human MHC type I antibody amidst the mouse recipient explant culture or animal. Alternatively, (2) FACS-purified LGR5$^+$ ISC can undergo infection with lentivirus GFP for 2-6 h, prior to downstream use.

B. Assay of Stem/Progenitor Activity of the LGR5+ Versus LGR5− Fractions.

Figure 12:
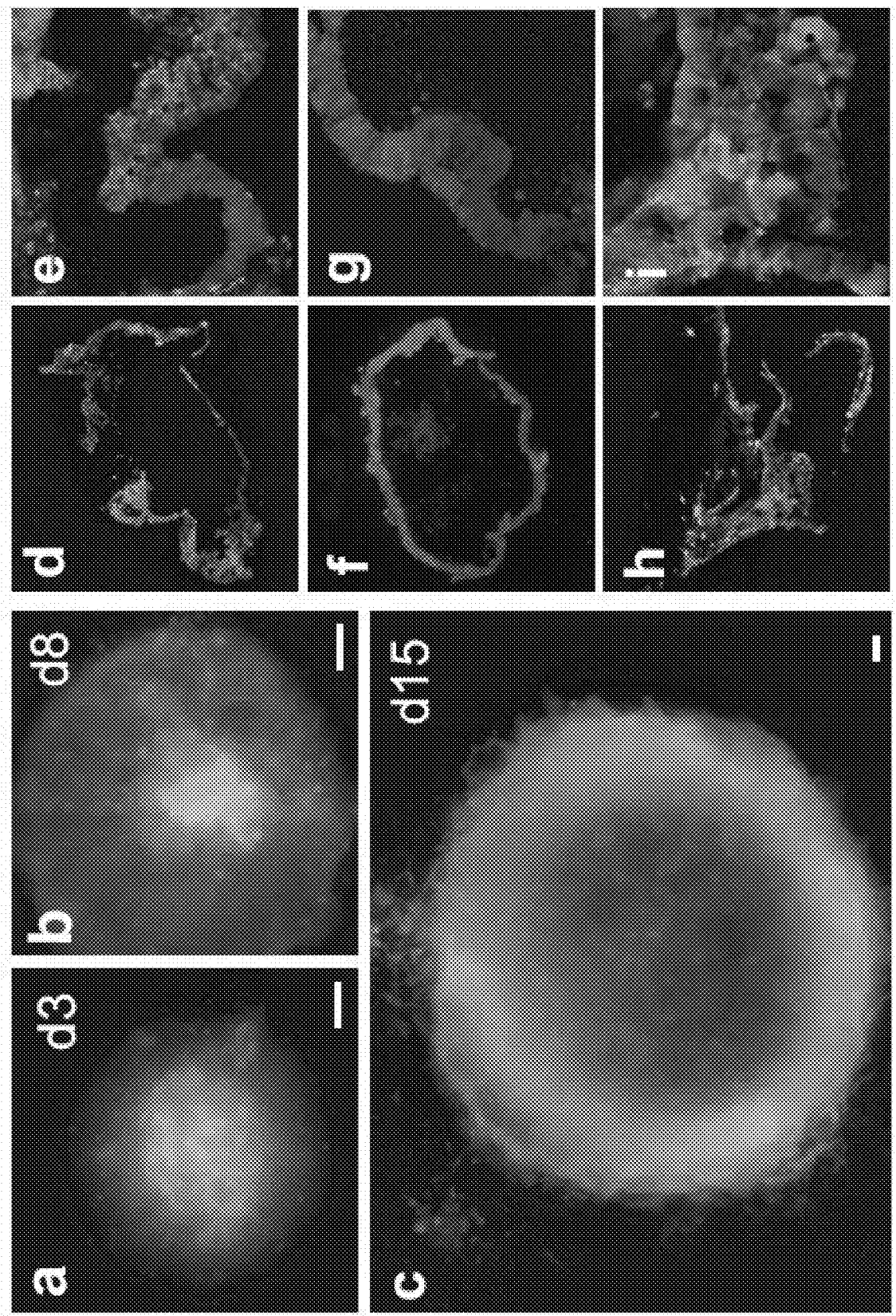
FIG. 12A-12I Clonal analysis of intestinal spheres from multicolor tetrachimeric mouse intestine.

Stem/progenitor activity of the LGR5$^+$ versus LGR5$^-$ fractions is assayed in vitro by injection into murine colon explant cultures which we have demonstrated to accurately recapitulate the Wnt- and Notch-dependent ISC niche. Briefly, neonatal mouse colon is minced and placed into a collagen type I gel matrix within a large (60 mm$^3$) transwell and cultured with Ham's F-12 medium with 20% FCS. We have recently developed methodology in which GFP marked LGR5$^+$ tumor cells can be successfully microinjected and incorporated into these cultures (FIG. 12). Here, colon LGR5$^+$ versus LGR5$^-$ cells from normal or IBD human colon (see below) are microinjected into the intestinal explant cultures followed by observation over a 30-100 day period. Ideally, the number of injected cells is downwardly titrated to the extent where limiting numbers or even single GFP-marked LGR5$^+$ cells can be introduced into the ISC niche of the explant cultures. As described above, alternative tracking of the human LGR5+ ISC can be performed with anti-human MHC type I.

Seminal characteristics of stem/progenitor cells include continued self-renewal, proliferation and multilineage differentiation. The proliferative activity of GFP labeled LGR5$^+$ versus LGR5$^-$ cells within the explant ISC niche is monitored over the 30-100 day period by double fluorescence of GFP and PCNA/BrdU. Multilineage differentiation within the introduced GFP$^+$ LGR5$^+$ cells will be demonstrated by co-localization of GFP with anti-mucin (goblet) and in the case of small intestinal LGR5$^+$ cells, additionally with enteroendocrine or Paneth markers.

A. Wnt-Dependent Ex Vivo Expansion.

Human LGR5$^+$ ISCs are purified by FACS as described above, and injected into murine neonatal colon explant culture. Subsequently, the murine colon explants with injected human LGR5$^+$ ISCs are cultured in the presence or absence of recombinant R-Spo1 (500 ng/ml). The human LGR5$^+$ cells are monitored either by lentiviral GFP signal or anti-human MHC immunoreactivity for R-spondin-dependent expansion. Alternatively, FACS analysis for human LGR5$^+$ GFP$^+$ cells is performed to precisely quantitate the percentage of human LGR5$^+$ cells within the explant and modulation of this ratio by R-Spondin, as well to accurately enumerate the LGR5$^+$ cells with and without R-spondin treatment. Proliferation and multi-lineage differentiation within the GFP$^+$ human LGR5$^+$ cells is measured as above.

Example 4

We describe a robust long-term methodology for either small or large intestinal culture, incorporating a physiologic air-liquid interface and underlying stromal and myofibroblast elements.

These cultures demonstrated growth for a range of 30 to >350 days as spheres with maintenance of both proliferation and multi-lineage differentiation. Notably, explant growth was both inhibited by the Wnt inhibitor Dickkopf-1 (Dkk1), and markedly stimulated by the Wnt agonist R-Spondin1 (RSpo1). Furthermore, the γ-secretase inhibitor dibenzazepine (DBZ) induced whole-scale goblet cell differentiation, consistent with endogenous Notch function, while adenoviral expression of neurogenin-3 (Ngn3) was sufficient to induce enteroendocrine cell differentiation.

The explants possessed clonal domains as well as LGR5+ ISC, while exhibiting lack of long-term repopulation following transient Dkk1-mediated Wnt inhibition, consistent with the functional presence of Wnt-dependent ISC and/or long-lived TA cells. Our results indicate successful in vitro recapitulation of the Wnt- and Notch-dependent ISC niche, demonstrate successful long-term culture of the intestine within this microenvironment, and describe methodology with widespread application to general investigations of intestinal biology.

The surface of the intestine is lined by a simple columnar epithelium that undergoes complete regeneration every 2-7 days. Underlying this profound regeneration are intestinal stem cell (ISC) populations, including pan-intestine LGR5-positive ISC at the crypt/gland bases 9 and small intestine Bmi1-positive ISC at the crypt "+4" position. These ISC divide to produce transit amplifying (TA) cells, which migrate toward the lumen, differentiate into absorptive enterocyte, goblet, Paneth and enteroendocrine lineages, followed by either extrusion into the luminal surface or Paneth cell phagocytosis.

Stem cells are generally influenced by a microenvironmental niche, typically comprised of epithelial and mesenchymal cells and extracellular substrates, and which instructs either self-renewal or selective adoption of a particular cell lineage. The intestinal stem cell niche is notable for myofibroblasts adjacent to the crypt and gland bases, which are believed to elaborate paracrine signals regulating the neighboring ISC. Extracellular Wnt signals are absolutely required within the ISC niche as deduced from the rapid ablation of proliferation and secondary loss of differentiation observed with the secreted Wnt inhibitor Dkk1. Notch signals are similarly essential with stimulation amplifying the progenitor pool and inhibition resulting in large-scale conversion to post-mitotic goblet cells.

Studies of the intestine, whether related to stem cells or to more general questions of physiology, have been confounded by a notable lack of long-term methodology for primary culture. To study signals regulating self-renewal and proliferation of intestinal stem cells we established a primary mouse explant system retaining the cellular architecture of the ISC niche with mesenchymal myofibroblasts. Culture of either small or large intestine neonatal explants within a collagen gel with an air-liquid interface yielded expanding cystic structures with a lumen present on gross inspection by 7 days. Virtually all cultures exhibited growth for 30 days, with a spectrum up to 350 days in vitro observed (the longest time point examined).

The wall of the intestinal spheres consisted of a polarized epithelial monolayer with an apical, inner luminal surface, and a basal outer surface in close proximity to the basal epithelial surface and the collagen matrix. The intestinal epithelial cells exhibited not only high proliferative activity at extended time points but also multilineage differentiation including absorptive enterocytes, goblet cells, enteroendocrine cells, and Paneth cells. Ultrastructural examination revealed the fully differentiated microstructures of cultured intestinal epithelial cells including microvilli, mucus granules, and endocrine granules, as well as intracellular functional connections of junctional complexes.

Surprisingly, some of the intestinal spheres showed autonomous contraction within the outer lining muscle layer during culture days 5-14. Culture growth was most prolonged with explants from postnatal days 0-2, although it was possible to culture small and large intestine up to postnatal days 7 and 28, respectively. The air-liquid interface was absolutely essential for growth in this system.

As Wnt signaling promotes maintenance of epithelial stem cells and early progenitor compartments, we hypothesized that the long-term growth of the intestinal explants would be modulated by alteration of Wnt signals in vitro. We previously demonstrated that Dickkopf-1 (Dkk1)-dependent Wnt inhibition produces rapid cessation of intestinal epithelial proliferation and crypt loss in the adult, consistent with findings in non-conditional villin-Dkk1 mice.

Accordingly, we treated d28 pre-established small or large intestine spheres with Dkk1 for an additional 5d, resulting in rapid degeneration of the epithelial layer. Similarly, addition of recombinant Dkk1 into the culture media at the time of plating resulted in dose-dependent growth inhibition. Conversely, to achieve gain-of-function Wnt activation, we utilized R-spondin1 protein (RSpo1), which strongly augments intestinal proliferation in vivo. Treatment with an RSpo1-Fc fusion protein produced a significant increase in the number and size of intestinal spheres, with a marked increase of PCNA-positive proliferating cells. These studies with both Wnt gain and loss-of-function indicated both accurate recapitulation of the Wnt-dependent ISC niche in culture, as well as Wnt responsiveness of the cultured intestinal epithelium.

Notch genes encode large, single-transmembrane receptors regulating a broad spectrum of cell fate decisions; in the intestine, Notch governs secretory lineage fate and maintains the proliferative progenitor state. Notch inhibition with γ-secretase inhibitors 22 or by conditional targeting of RBP-Jk both induce dramatic goblet cell hyperplasia in vivo. Accordingly, treatment of pre-established small intestine explants with the γ-secretase inhibitor dibenzazepine (DBZ) for 5 days produced complete replacement of the epithelial layer by terminally differentiated goblet cells, by morphology, PAS positivity, and absence of mitotic PCNA staining. Identical results were observed with DBZ treatment of large intestine explants.

These results suggested accurate ex vivo recapitulation of the Notch-dependent ISC niche within the intestinal sphere culture. The plasticity of the intestinal sphere cultures was further examined with respect to the enteroendocrine lineage. The helix-loop-helix transcription factor Neurogenin 3 (Ngn3) regulates enteroendocrine fate, with overexpression increasing intestinal enteroendocrine cell number. Adenoviral Ngn3 overexpression in duodenal explants was sufficient to induce an approximately 3-fold increase in Chromogranin A-positive enteroendocrine cells versus a control adenovirus expressing an antibody IgG2(Fc fragment. Both the Ngn3 induction of enteroendocrine cells and DBZ induction of goblet cells argue for significant plasticity of the cultured epithelium, and possible viral or small molecule approaches thereof.

Figure 13:
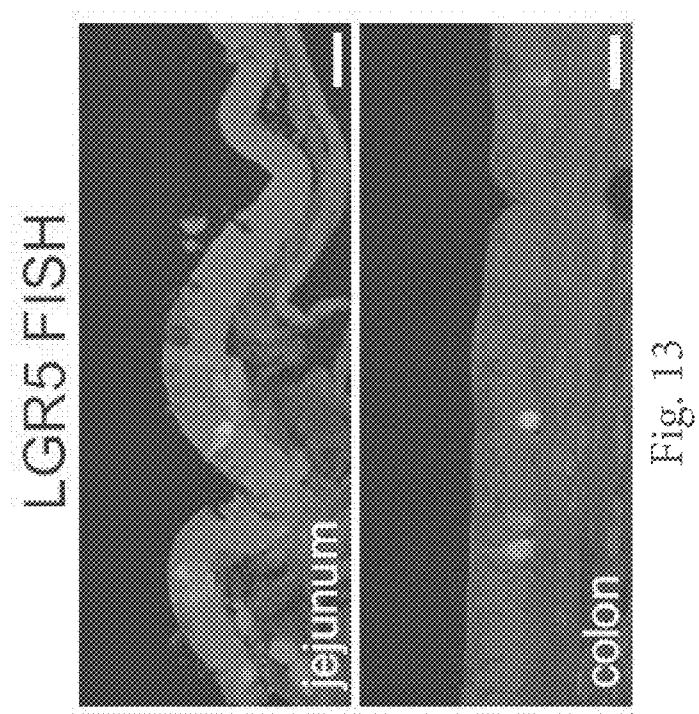
FIG. 13. Explant cultures contain LGR5-positive ISC. Fluorescent in situ hybridization for LGR5 is depicted at culture d35.

The prolonged expansion and proliferation within the intestinal explant sphere cultures (>300 days) strongly suggested the robust support of ISC. Mosaic analyses of developing intestine have revealed that intestinal epithelium is initially generated as a well-mixed population of multiple progenitors at birth which becomes exclusively monoclonal within each crypt by P14, suggesting specification of ISCs by the niche during this period. Accordingly, intestinal explants from tetrachimeric mice with mosaic expression of distinct fluorescent proteins exhibited progressively demarcated clonal fluorescence domains consistent with ISC specification (FIG. 12a-i). The presence of ISC was corroborated by the presence of rare LGR5-expressing populations in explant cultures using fluorescent in situ hybridization (FIG. 13j). Extracellular Wnt signals are essential for maintenance of the intestinal proliferative compartment, acting on either ISC themselves and/or downstream transit-amplifying progenitors.

The analysis of intestinal repopulation kinetics after acute Wnt inhibition in vivo have been precluded by the rapid lethality of Ad Dkk1-treated mice, and the apparent continued epithelial regeneration allowing survival of villin-Dkk1 mice. To overcome these limitations, the intestinal sphere culture, containing LGR5+ ISC within a rigorously Wnt-dependent niche, was exploited as a surrogate functional in vitro approach. Accordingly, newly plated cultures were treated with Dkk1 or vehicle for 7d, followed by long-term observation without Dkk1. Under these conditions, transient Dkk1 exposure was sufficient to ablate culture growth even over a subsequent 35-day observation period without Dkk1 (the longest period tested) (FIG. 14k). Intestinal epithelial cells were selectively absent while remnant myofibroblasts were still present, consistent with similar epithelial tropism of Ad Dkk1 in vivo.

Combined with the very long duration of explant growth (>300 days) these results are consistent with a model in which Wnt signaling is required for maintenance of ISC and/or of extremely long-lived TA cells. The lack of long-term methodology for primary intestinal culture has been a substantial obstacle to exploration of intestinal stem cell biology and more general questions of physiology. In contrast to prior efforts, the explant method described herein permits for the first time sustained intestinal proliferation and multi-lineage differentiation over a range of 30 to >350 days.

Relevant features include the incorporation of an air-liquid interface similar to that encountered by the intestine in vivo, as well as the inclusion of outer lining myofibroblasts and stromal elements which have been postulated to represent crucial elements of the ISC niche. Notably, the intestinal sphere cultures accurately recapitulated the Wnt- and Notch-dependency of the ISC niche in vivo, with Dkk1 and DBZ treatment phenocopying in vivo Wnt and Notch inhibition. At the same time, the endogenous Wnt and Notch signaling within explant cultures was sufficient to support vigorous expansion of the intestinal sphere cultures in the absence of exogenously added agonists of these pathways. This preservation of the ISC niche likely underlies the successful support of long-term proliferation and differentiation observed in the current studies.

The prolonged growth and differentiation (>300 days), as well as the absence of repopulation after transient Wnt inhibition, suggest the primary action of Wnts on either ISC and/or of extremely long-lived TA cells. Overall, the availability of a robust intestinal culture system possessing ISC and accurately recapitulating the ISC niche in both small and large intestine will greatly facilitate the study of intestinal stem cells and niche-ISC interactions. This model can be also potentially used to study intestinal epithelial interactions with other heterologous cell types, including neurons, endothelial cells and immune cells. Further, the enablement of primary intestinal culture will have widespread application to general studies of intestinal biology, including investigations of physiology, host-pathogen interactions, neoplasia and tissue engineering.

Example 5

Here we describe a robust long-term methodology for primary mouse intestinal culture allowing sustained intestinal proliferation and multilineage differentiation over a range of 30 to >350 d, using both neonatal and adult tissue as starting material. Defining characteristics include the use of an airliquid interface coupled with a 3D culture matrix, as well as recapitulation of both the cellular myofibroblast architecture and the rigorous Wnt and Notch dependence of the ISC niche. We further exploit this methodology to show the presence of putative ISC populations within these cultures and their in vitro modulation by the Wnt agonist RSpo1-Fc. These studies describe a method to enable study of both ISCs and the ISC niche, as well as general investigations of intestinal biology.

We have been able to use small and large intestine from juvenile or adult mice up to 26 weeks of age (the oldest age evaluated) as starting material (FIG. 15A-15J). Our studies indicate that their viability may be less extensive than with neonatal cultures. Regardless of the age of the mouse cells used for the intestinal culture, both proliferative zones and differentiated zones were present. Whereas proliferative zones were commonly observed within areas of monolayer within 2 weeks, crypt-like structures were also often produced within both small and large intestinal spheres (FIG. 15A-15J). Furthermore, villus-like protrusions were occasionally present in the jejunal spheres (FIG. 15B). The crypt-like structures showed marked proliferative activity; in contrast, the villus-like structures or differentiated zones were devoid of proliferating cell nuclear antigen (PCNA)-positive cells (FIG. 15C,15D). Accumulation of apoptotic sloughed cells positive for single stranded DNA in the sphere lumen and BrdU pulse labeling revealed the rapid turnover and proliferation of intestinal epithelial cells in culture.

FIG. 15A-15J shows intestinal cultures from juvenile and adult mice. FIGS. 15A-15H show the histology of jejunal culture at day 7 from 3-week-old (FIG. 15A-15F) or 26-week old mice (FIG. 15G15H). Staining for H&E in FIG. 15A,15B,15G,15H, PCNA (FIG. 15C,15D) or CD44 (FIG. 15E,15F) is depicted. (FIG. 15I,15J) RSpo1-Fc treatment permitted longer term jejunal culture (day 28) from 8-week-old adult intestine. Stereomicroscopy (FIG. 15I) and H&E staining (FIG. 15J) is depicted. Arrows indicate highly proliferative, PCNA+ crypt-like structures, which invaginated from the sphere wall into the surrounding collagen matrix. Arrowheads indicate quiescent PCNA-villus-like protrusions. Numerous sludged or dead cells are present in the sphere lumen, indicated by the asterisk.

Methods

Animals and Mouse Embryonic Stem Cells.

Mice were bred and maintained at the Stanford University Research Animal Facility in accordance with Stanford University guidelines. C57Bl/6 neonatal mice aged 0-2 days were used throughout. Rosa 26 knock-in ES clones carrying mOrange or mCherry (BD Clontech) were generated as described. Tetrachimeric mice were generated by injection of Rosa 26 knock-in ES clones (ECFP, mOrange and mCherry) into Rosa 26 EGFP blastocysts.

Three-Dimensional Explant Culture System. The mouse small and large intestine (optimally postnatal days 0-2) was opened lengthwise and washed in PBS to remove all luminal contents. A 1 cm segment was minced immediately and extensively on ice with iris scissors. The minced tissues were embedded in a three-dimensional collagen gel using a double-dish culture system. A 1 ml collagen gel solution (Nitta Gelatin Co.) was poured into a 30-mm dish (Millicell-CM, Millipore Co.), the inner dish, with a nitrocellulose bottom to form an acellular layer. Next, a 1 ml collagen gel solution containing a total of 0.1 g minced tissues was placed on the acellular layer in the dish. This inner dish was placed into a 90-mm outer dish containing 10 ml Ham's F12 supplemented with 20% FCS and 50 µg/ml gentamicin. The culture assembly was carried out for 7-365 days at 37 C in a humidified atmosphere of 5% $CO_2$ in air, and the medium was changed every 7 days. Where appropriate, murine RSpo1-Fc, Dkk1 or DBZ (Calbiochem) were included in the outer dish medium at 500 ng/ml, 0.5-50 µg/ml and 10 µM respectively with change of medium every 1-2 days.

Protein Purification.

The murine R-spondin-1-Fc fusion protein containing a C-terminal murine antibody IgG2a Fc fragment and murine Dkk1 bearing a N-terminal HA-tag and C-terminal FLAG and 6×His tags were purified from the conditioned medium of stably transfected 293T cells using protein A affinity and Ni-agarose chromatography, respectively.

Detailed Protocol for Explant Culture 1.

This culture system maintains the cultured cells embedded in the collagen gel under an air-liquid interface environment. Before preparing the tissue, an inner dish with collagen gel bottom layer should be made. The following procedure is done using Cellmatrix type I-A (Nitta Gelatin Inc.) as a premixed type I collagen gel, however, other products are able to use as an extracellular matrix, such as matrigel. The inner dish should have permeable and/or pored membrane bottom, such as a cell culture insert. We typically use Millicell culture plate inserts (Millicell-CM, Millipore Co.) or Falcon cell culture inserts (BD Co.) as the inner dish. All the following material scale/volume are variable and should be selected in accordance with the intended use. For example, a 1 ml of collagen gel solution is poured into a 30-mm diameter inner dish in combination with 60 mm diameter outer dish and 2 ml of culture media. If 10-mm diameter inner dish is applied, 0.3 ml of collagen gel solution is pored into the inner dish in combination with a 24-well outer dish and 0.5 ml of culture media. The inner dish is ready to use after the gel solidifies (see below).

Small or large intestine is removed from neonatal mice, with aseptic procedure. Postnatal day 0-2 intestine grows most vigorously although we have had success with small and large intestine up to postnatal days 7 and 28. The removed tissue (typically 1 cm) is immediately immersed in ice-cold PBS or other culture media/tissue preservative solution such as Ham's F12 medium without serum. The small intestine or colon are opened lengthwise and washed in ice-cold PBS (or other solution mentioned above) to remove all luminal contents.

The washed tissue is minced by iris scissors etc. on ice-cold plate such as a tissue culture plate lid. The final minced tissue has heterogenous size, but under 0.1 mm3 is suitable for culture. The tissue should be minced extensively so as to have an almost viscous appearance. This procedure should be done within 5 minutes to avoid cell damage and drying the tissue. The minced tissue is mixed in ice-cold, pre-solidified collagen gel solution.

The cell-containing collagen gel is poured onto the inner dish prepared in step 1. The inner dish is placed in the outer dish. The gel easily solidifies at 37° C. within 30 minutes. After solidifying the cell-containing gel, the culture media is pored into the outer dish. For a 1 ml of collagen gel solution is poured into a 30-mm diameter inner dish, 2 ml of culture media should be added into the 60 mm diameter outer dish. At this point, the cultured cells should not be immersed in culture media. The cellular gel layer should exist above the medium level to create the air-liquid interface microenvironment.

Variable solution and antibiotics can be used for culture media. We use Ham's F12 supplemented with 20% fetal calf serum and 50 µg/ml gentamicin. Variable substances such as protein or drug can be added in the culture media. The culture assembly is carried out over 30 to >350 days at 37° C. in a humidified atmosphere of 5% $CO_2$ in air. Medium is changed every 7 days, but the frequency may depend on cell numbers and if labile test growth factors are being added. Living culture cells can be observed by phase-contrast microscopy or stereo microscopy.

For histological analysis, the culture assembly can be fixed with variable solutions such as 4% PFA and embedded in paraffin. Deparaffinized cross sections can be stained with variable staining methods such as hematoxylin and eosin. Deparaffinized sections are able to be use for immunohistochemistry for variable antibodies. For ultrastructural analysis by transmission electron microscopy, the culture assembly can be fixed with 2.5% glutaraldehyde and 1% osmic acid, dehydrated with alcohol, and embedded in epoxy resin.

A variety of drugs/proteins/cytokines can be tested in cultured cells. For example, growth of cultured intestinal cells is promoted by Wnt agonist R-Spondin1, and is inhibited by Wnt inhibitor Dickkopf-1 (Dkk1). The treatment with γ-secretase inhibitor dibenzazepine (DBZ) leads to whole-scale conversion to a goblet cell phenotype. These are typically added to the outer chamber.

Adenoviral Infection of Explant Cultures. Ad Ngn3 was a kind gift of from Mark Kay. Ad Fc encoding an antibody IgG2γ Fc fragment has been described. $1 \times 10^8$ adenoviral particles in 0.25 µl PBS were microinjected into the lumen of pre-established spheres using glass-pulled pipettes. Addition of adenovirus to the outer chamber appears to work as well in control Ad GFP experiments.

TOP FLASH luciferase assay. RSpo1-Fc (500 ng/ml) and Wnt3a L cell (gift of Roel Nusse) conditioned medium (1:2 dilution) were added to serum-starved 293T TOP FLASH cells (gift of James Chen) in 200 µl in 96-well format. After 48 h, firefly luciferase expression was determined using a Dual Luciferase Reporter Assay Kit (Promega). Activity was normalized to a Renilla reporter.

In situ hybridization T7 promoter incorporated primers were used to generate a mouse LGR5 DNA template from E14.5 mouse embryo cDNA. Both Dig-labeled sense and antisense probes were generated by in vitro transcription using T7 polymerase. The probe spans nt 1484-2101 based upon GenBank accession NM_010195. Tissue was fixed with 4% PFA and embedded in paraffin. Sections were processed by deparaffinization, rehydration, 0.2M HCl treatment, proteinase K digestion, and acetylation. Samples were hybridized with probes at 68° C. overnight in humidified chamber containing 5×SSC, 50% formamide, Following stringent washing with 2×SSC, 50% formamide for 3×20 min, samples were rinsed in TBST and incubated with anti-DIG-POD (Roche, 1:500) overnight. Cy3 tyramide (1:100 in amplification diluent) was applied in order to visualize LGR5 transcripts.

Histology and Immunohistochemistry

Cultures were fixed with 4% PFA overnight, paraffin-embedded and sectioned. Deparaffinized cross sections were stained with hematoxylin and eosin (H&E) and alcian blue (Al-B). The following antibodies were used: mouse anti-rat monoclonal proliferating cell nuclear antigen (PCNA, Dako), anti-chromogranin A (Zymed) and antilysozyme (Dako). Deparaffinized sections were immunostained by the avidin-biotin complex immunoperoxidase (ABC) method. For frozen sections, cultures were fixed in 4% paraformaldehyde at 4° C. Then cultures were washed with PBS, cryoprotected overnight in 30% sucrose, and quick-frozen in optimum cutting temperature (OCT) compound. Frozen sections (5-7 micron) were cut at −20° C. from OCT-embedded tissues using a microtome (Bright Instruments, Huntingdon, U.K.). For transmission electron microscopy, samples were fixed with 2.5% glutaraldehyde and 1% osmic acid, dehydrated with alcohol, embedded in epoxy resin followed by visualization (JME-1210, JEOL, Tokyo, Japan).

Statistical analysis Data obtained from six to nine independent experiments were analyzed by student's T test. Results were expressed as means±SEM and were considered significant with P values of <0.05.

Example 6

Screening for Notch/γ-Secretase Inhibitors

The self-renewing epithelium of the small intestine is ordered into stem/progenitor crypt compartments and differentiated villus compartments. Recent evidence indicates that the Wnt cascade is the dominant force in controlling cell fate along the crypt-villus axis. A rapid, massive conversion of proliferative crypt cells into post-mitotic goblet cells has been found after conditional removal of the common Notch pathway transcription factor CSL/RBP-J. Similar phenotype was obtained by blocking the Notch cascade with a γ-secretase inhibitor.

Figure 8:
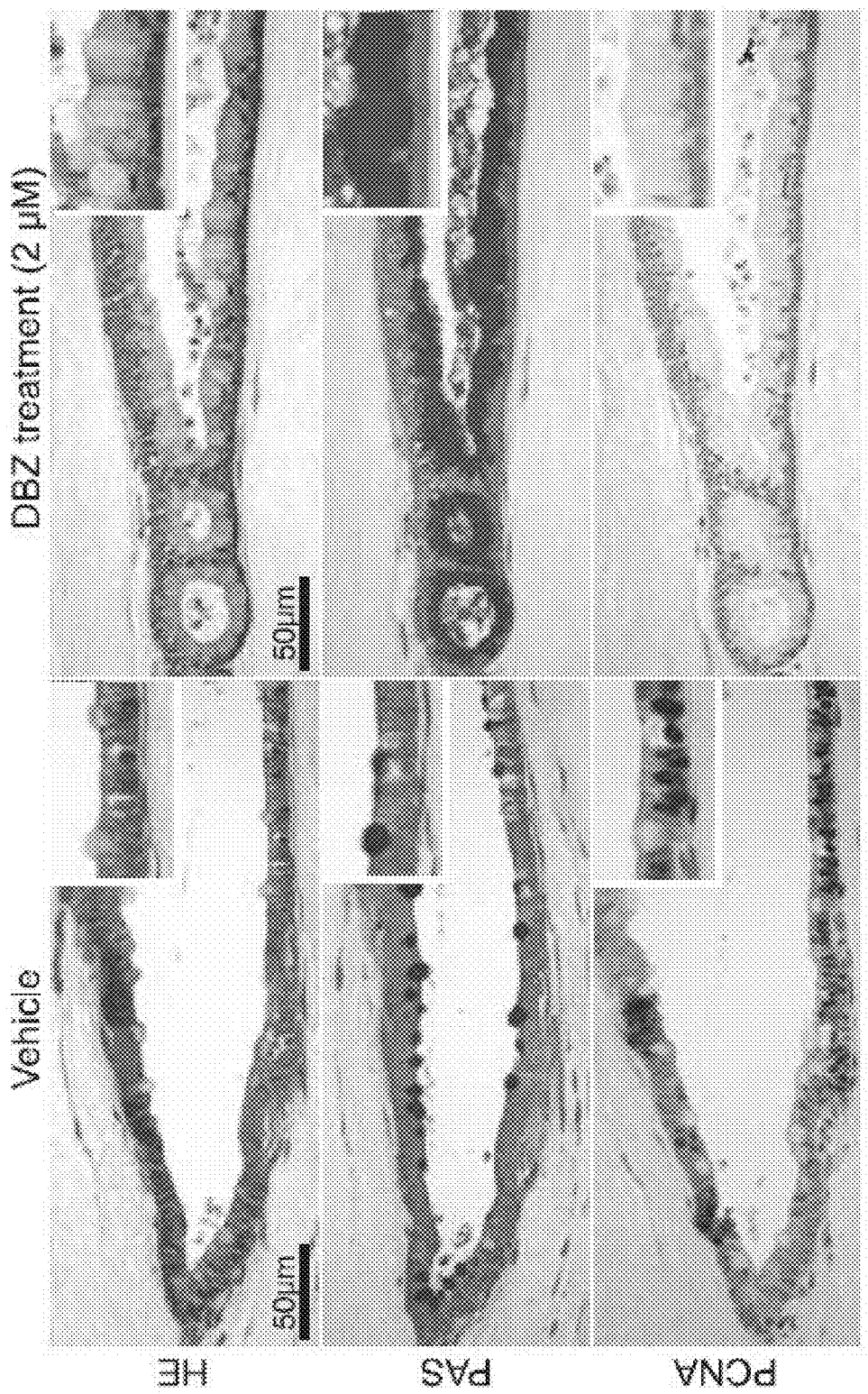
FIG. 8. Notch/γ-secretase inhibitor DBZ induces goblet cell conversion of cultured intestinal epithelium. Jejunal explant cultures were established for 7 days followed by 5 days treatment with 2 µM DBZ. Note virtually quantitative conversion of jejunal epithelium to post-mitotic goblet cells.
Figure 9:
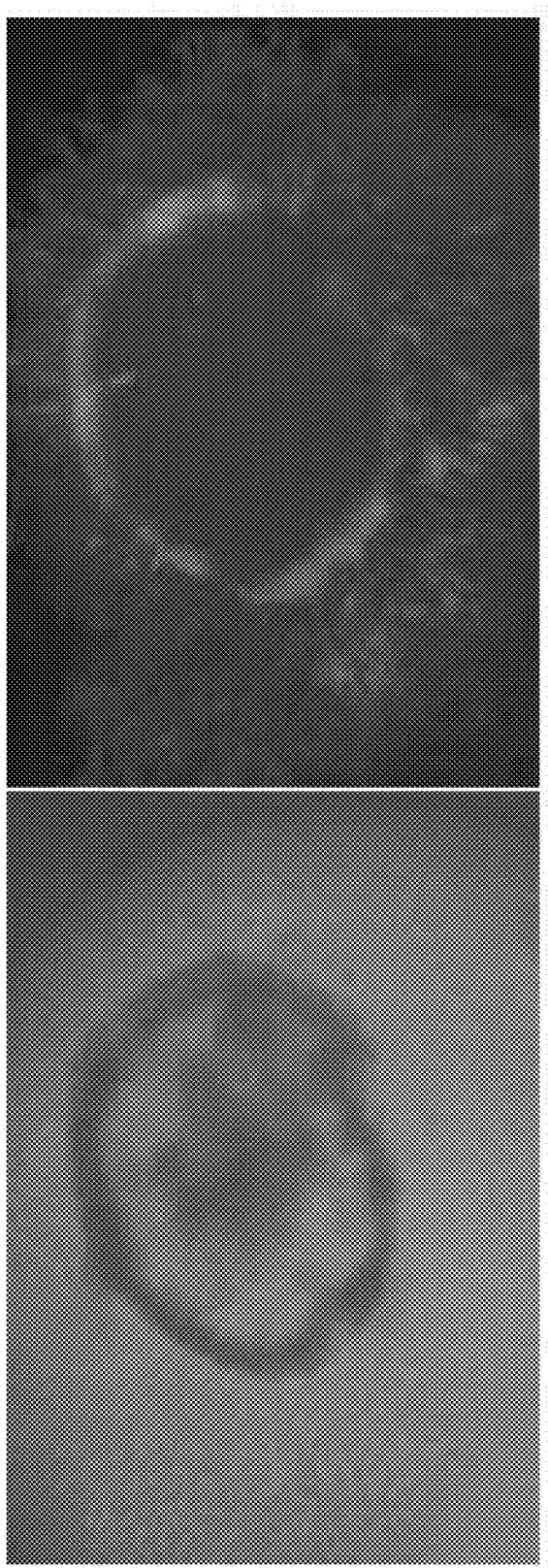
FIG. 9. Fluorescent images of intestinal spheres from C57Bl/9 mice transduced with GFP adenovirus vector (Left—brightfield, right—fluorescence).

We have demonstrated active Notch signaling in the intestinal explant cultures as treatment with the γ-secretase inhibitor DBZ leads to whole-scale conversion to a goblet cell phenotype in colon (FIG. 8) and small intestine, phenocopying in vivo results from other groups.

This phenotype is used to screen for inhibitors of Notch/γ-secretase activity. Intestinal explant cultures (about 7 days old) are exposed to candidate agents or vehicle for about 5 days. 2-5 µM DBZ is used as a positive control. The cultures are then analyzed for the presence of increased number of goblet cells, using either PCNA or PAS (periodic acid-Schiff) staining. Increased number of goblet cells is indicative of inhibition of Notch activity.

Example 7

Colorectal cancers can be classified as having either chromosomal instability (CIN, 85%), or microsatellite instability (MSI/MIN/replication error/RER, 15%). The genetic events underlying CIN colorectal cancers are understood to occur through an ordered sequence of mutations. Initiating mutations resulting in the formation of polyps occurs in the Wnt pathway, typically with APC loss-of-function "driver" mutations, followed by subsequent nuclear accumulation of β-catenin and constitutive activation of the β-catenin/TCF4/LEF transcriptional complex. This primacy of colon cancer Wnt/APC mutations parallels Wnt action as a dominant and essential regulator of proliferation in the non-neoplastic intestinal crypt stem cell compartment. Subsequently, other critical driver mutations follow, e.g., in KRAS, TP53 and others, ultimately resulting in invasive and metastatic CRC. MIN colorectal cancers exhibit microsatellite instability from lesions in DNA mismatch repair genes such as hMSH2, hMLH1, hMSH6, and/or PMS2, which lead to mutation in numerous downstream genes including but certainly not limited to CIN genes.

In addition to the aforementioned relatively rare, high-penetrance variants, array CGH and genome-wide association SNP analyses have revealed deletion and/or linkage to 11q23, 8q24 and 18q21, although the causative mutations have not been functionally identified. These studies have revealed common sequence variations that significantly predispose to early CRC, and portend poor outcome. Whole-genome sequencing studies have confirmed known genes such as APC, KRAS and TP53 most commonly mutated and with highest probability of representing driver mutations, while documenting hundreds of additional candidate genes.

The functional validation of the minority of driver oncogenes amongst hundreds if not thousands of mutated genes has proven a significant challenge. A significant obstacle to rapid functional validation of novel CRC loci has been that it has been heretofore impossible to initiate carcinogenesis in vitro from primary colon tissue, much less to perform in vitro observation and genetic manipulation thereof. This has been in no small part due to the fact that it has been heretofore impossible to culture primary intestinal epithelium for any appreciable amount of time.

The methods of the present invention have now allowed the use of an in vitro culture system to achieve the first in vitro transformation of primary intestinal epithelium to cancer. Using cultures from $APC^{flox/flox}$; villin-CreER mice, tamoxifen-dependent APC deletion can be easily achieved in vitro, yielding a non-invasive but hyperproliferative intestinal epithelium. However, infection of these APC-null cultures with retrovirus encoding either RasG12D as a prototypical dominantly acting oncogene, or p53 shRNA as a model tumor suppressor, contributes a "second hit" that induces wholesale in vitro neoplastic transformation and invasion within 10-20 days.

This validated system is used to perform functional screening of novel CRC oncogenes and tumor suppressors from whole genome sequencing databases, for example in the context of an APC-null background.

Our newly developed culture methodology represents a powerful tool to modeling intestinal carcinogenesis in vitro. APC mutations occur early in the colon adenoma-carcinoma sequence and are permissive for further transforming mutations. One strategy thus utilizes our culture system to investigate effects of candidate tumor suppressors and oncogenes in an APC-setting using tamoxifen-treated Villin$^{Cre-ER}$; $APC^{flox/flox}$ (thus APC-null) primary intestinal cultures. To model simple APC deletion in vitro, tamoxifen-treated Villin$^{Cre-ER}$; $APC^{flox/flox}$ cultures manifested APC loss and orderly hyperproliferation without gross dysplasia or invasion.

Additional oncogenic hits in CRC, such as in KRAS or TP53, are believed to occur in the setting of baseline APC loss-of-function mutations. In vivo, this multi-hit schema for colon carcinogenesis has been effectively modeled in mice, where additional genetic lesions such as KRAS mutations dramatically synergize with APC loss to induce adenocarcinoma. Accordingly, we developed a method to transduce the APC-null intestinal cultures by microinjection of retrovirus into the lumen of the intestinal spheres; for example using retrovirus GFP we obtained ~100% infection. We then modeled the effects on APC-null cultures of subsequent retroviral expression of either (1) activated Ras$^{G12D}$ as a prototypical dominantly acting oncogene, or (2) p53 shRNA, simulating a loss-of-function tumor suppressor.

Retrovirus Ras$^{G12D}$ infection of the APC-null tamoxifen-treated Villin$^{Cre-ER}$; $APC^{flox/flox}$ cultures resulted in a striking morphologic transformation with a stratified epithelial layer many cell layers thick, prominent nuclear enlargement with marked atypia, as well as robust invasion into the surrounding collagen, all evident within 20 days of retroviral infection. In contrast, control retrovirus GFP infection (i.e. APC-null alone) was not associated with such changes, with cultures exhibiting a hyperproliferative, although well-organized, stereotyped epithelial monolayer organization.

Efficient morphologic transformation of primary intestine cultures with APC deletion and Ras$^{G12D}$. Primary small intestine cultures were established from Villin$^{Cre-ER}$; $APC^{flox/flox}$ mice and pre-established for 3 weeks with tamoxifen to effect APC deletion. At this time, either ecotropic retrovirus encoding Ras$^{G12D}$ or a control retrovirus GFP were microinjected into the lumen of the intestinal spheroids and cultured for an additional 20 days, followed by harvest for H&E staining.

Ras$^{G12D}$ induces basement membrane invasion in vitro. To detect the intestinal epithelial basement membrane, Laminin immunofluorescence was performed on 3-week-old tamoxifen-treated Villin$^{Cre-ER}$; APC$^{flow/flow}$ intestinal cultures. While an intact laminin-positive basement membrane underlies non-infected, APC-null intestinal epithelium, laminin staining was absent in the grossly dysplastic retrovirus Ras$^{G12D}$-infected cultures, indicative of basement membrane invasion in vitro.

In modeling tumor suppressors, we achieved essentially identical results with a well-documented retrovirus encoding shRNA against p53. This retroviral construct, LMP-p53.1224, expresses p53 shRNA from the context of microRNA flanking sequences, allowing for extremely efficient intracellular processing of the p53 shRNA and robust gene knockdown. Here, retrovirus encoding p53 shRNA, but not retrovirus GFP, again produced rapid morphologic transformation of tamoxifen-treated Villin$^{Cre-ER}$; APC$^{flox/flow}$ cultures from an organized epithelial monolayer into a frankly dysplastic tissue again with cellular stratification, pronounced nuclear enlargement and atypia, and invasion, all within 10 days.

These results utilizing Ras$^{G12D}$ and p53shRNA thus validate crucial positive controls for the use of the primary intestinal epithelial culture system of the invention to model the action of candidate oncogenes and tumor suppressors in the context of APC loss-of-function. Such in vitro methodology for modeling CRC oncogenes/tumor suppressors in primary intestinal culture has not previously existed, and will allow the rapid functional screening of candidate CRC oncogenes from whole genome sequencing databases, allowing categorization as driver versus passenger mutations.

Efficient morphologic transformation of primary small intestine cultures with APC deletion and p53 shRNA. Primary small intestine cultures from Villin$^{Cre-ER}$; APC$^{flox/flox}$ mice were pre-established for 3 weeks with tamoxifen to effect APC deletion. At this time, either retrovirus encoding p53 shRNA (LMP p53.1224) or control retrovirus GFP (LMP) were microinjected into the lumen of the intestinal spheroids and cultured for an additional 10 days, followed by harvest for H&E staining. Candidate genes include the highly ranked APC, KRAS and TP53, and genes with known functional relevance to CRC biology, such as PIK3CA, FBXW7, PTEN and SMAD2/4. Candidate oncogenes without prior known functional relevance to CRC include CSMD3 (transmembrane receptor), TNN (FN/EGF repeat), NAV3 (UNC53-like), the MAP kinase MAP2K7, tyrosine kinases EPHB6 and EPHA3, GUCY1A2 (guanylate cyclase), and RET (tyrosine kinase).

For a gene of interest retroviruses are created with IRES GFP encoding (1) full-length protein, (2) mutant alleles, and (3) shRNA. The cDNA encoding full-length protein and the mutant alleles is human, while the shRNA is mouse, given the mouse intestinal explant culture system. Tamoxifen-treated Villin$^{Cre-ER}$; APC$^{flox/flox}$ cultures are preestablished for ~20 days prior to microinjection of retrovirus. The LMP p53.1224 virus encoding shRNA against p53 is used as a positive control tumor suppressor, retrovirus Ras$^{G12D}$ as a positive control activated oncogene, and scrambled sequences as negative controls. Ecotropic retrovirus is produced in Phoenix cells, and the restriction of host range to mouse will circumvent biosafety issues with retroviruses encoding oncogenic loci. After 20 days, the retrovirus-infected cultures (tumor suppressor shRNA vs GFP control) are harvested for the following analysis:

Histology:

Gross evaluation of sphere size upon stereomicroscope examination will be performed. H&E staining of sections will be evaluated in regards to cellular morphology, including the presence of cellular stratification, nuclear pleiomorphism and atypia, and invasion. Mitotic index will be determined by PCNA staining. Invasion will be assessed by H&E as well as collagen IV and laminin basement membrane staining. Potentially, a driver tumor suppressor or oncogene is able to induce frank dysplasia in cooperation with the APC deletion, as we have shown above for both Ras$^{G12D}$ and p53 shRNA. Knockdown is confirmed by qPCR on RNA from the cultures and or Western blotting/immunofluorescence with appropriate antibodies.

In Vitro Correlates of Transformation:

Cells are retrieved from control versus candidate (cDNA/mutant/shRNA) cultures versus positive control (p53 shRNA or Ras$^{G12D}$) by collagenase digestion, and focus formation assays and growth in soft agar are used as functional readouts for transformation.

In Vivo Tumorigenicity:

The APC$^{flox/flox}$; villin-CreER mice are on a fully backcrossed C57Bl/6 background and thus cells from the cultures are transplanted s.c. into recipient C57Bl/6 mice to demonstrate in vivo tumorigenicity.

Cancer Stem Cell Phenotype:

We have developed antibodies recognizing the colon cancer stem cell antigen LGR5. These function in both immunostaining and FACS and are used to stain and purify colon cancer stem cells from the cultures, followed by in vitro and in vivo evaluation as above.

In one variation, the length of in vitro culture is prolonged to 100-200 days. The shRNA knockdown of candidate genes may be layered on top of APC deletion+Ras$^{G12D}$ expression and temporal acceleration of morphologic transformation assessed. Additional gene knockdown is added by multiple shRNA cassettes within the same retrovirus to add SMAD2, SMAD4 or DCC knockdown to other candidates.

Additional directions include functional validation of genes in amplicons and deletions, modeling of human CRC in human intestinal cultures using lentiviral cDNA/shRNA expression, drug screening in primary intestinal culture, unbiased overexpression or gene knockdown screens, combinatorial mutation modeling, and determination of effects of altering the temporal onset of CRC mutations.

What is claimed is:

1. A method for generating a long term culture of mammalian intestinal cells, wherein the culture this thus generated provides for multilineage differentiation that maintains (a) three-dimensional structure of intestinal epithelium and (b) differentiation markers characteristic of intestinal absorptive enterocytes, goblet cells and enteroendocrine cells, in which intestinal cells grow, differentiate and are viable for more than 3 months and up to 350 days, said culture comprising a primary intestinal tissue explant cultured in the presence of exogenous R-spondin; the method comprising:

initiating a culture by mixing fragments of a primary intestinal tissue with a gel solution;

pouring the gel solution mixed with fragments of the primary intestinal tissue over a layer of gel formed in a transwell container with a lower semi-permeable support;

placing the transwell in an outer dish comprising culture medium comprising exogenous R-spondin, wherein the level of the culture medium is maintained such that the gel containing the tissue is not submerged in the culture medium; and maintaining the long term culture for more than 30 days and up to 350 days; wherein cells in the resulting long term culture exhibit normal Wnt-signaling and are responsive to proteins that stimulate or inhibit intestinal growth, wherein the R-spondin is present at a concentration of from 500 ng/ml to 1 mg/ml.

2. The method of claim 1, wherein the explant is a cancer biopsy.

3. The method of claim 2, wherein the intestinal cancer biopsy explant comprises cancer stem cells.

4. The long term culture of claim 1, wherein the growth of intestinal cells is increased relative to cells in a culture in which R-spondin is absent.

5. The long term culture of claim 1, wherein the mammalian intestinal cells are experimentally modified prior to or during culture.

6. The method of claim 1 comprising analyzing long term proliferation growth of explants in the long term culture in the presence of a candidate drug, therapeutic antibody or protein-based therapeutic agent.

7. The method of claim 1, comprising analysis of multi-lineage differentiation of explants in the long term culture in the presence of a candidate drug, therapeutic antibody or protein-based therapeutic agent.

* * * * *